US009963667B2

(12) United States Patent
Loboda

(10) Patent No.: US 9,963,667 B2
(45) Date of Patent: May 8, 2018

(54) STRUCTURED BIOLOGICAL SAMPLES FOR ANALYSIS BY MASS CYTOMETRY

(71) Applicant: FLUIDIGM CANADA INC., Markham (CA)

(72) Inventor: Alexander V. Loboda, Thornhill (CA)

(73) Assignee: Fluidigm Canada Inc., Markham (CA)

( * ) Notice: Subject to any disclaimer, the term of this patent is extended or adjusted under 35 U.S.C. 154(b) by 0 days. days.

(21) Appl. No.: 14/986,431

(22) Filed: Dec. 31, 2015

(65) Prior Publication Data

US 2016/0194590 A1 Jul. 7, 2016

Related U.S. Application Data

(60) Provisional application No. 62/098,890, filed on Dec. 31, 2014, provisional application No. 62/108,911, filed on Jan. 28, 2015.

(51) Int. Cl.
*C12M 1/12* (2006.01)
*G01N 1/28* (2006.01)
(Continued)

(52) U.S. Cl.
CPC ............ *C12M 25/00* (2013.01); *G01N 1/286* (2013.01); *G01N 33/4833* (2013.01); *H01J 49/0027* (2013.01); *H01J 49/04* (2013.01); *G01N 2001/045* (2013.01); *G01N 2001/2886* (2013.01)

(58) Field of Classification Search
USPC ........................................ 250/288, 281, 282
See application file for complete search history.

(56) References Cited

U.S. PATENT DOCUMENTS 6,639,217 B1 10/2003 Li
7,586,091 B2 9/2009 Takahashi et al.
(Continued)

FOREIGN PATENT DOCUMENTS

WO 2014/031997 2/2014
WO 2014/169294 10/2014
WO 2014/169394 10/2014

OTHER PUBLICATIONS

Brückner et al., DNA Quantification via ICP-MS Using Lanthanide-Labeled Probes and Ligation-Mediated Amplification, Anal. Chem. vol. 86(1), Jan. 7, 2014, pp. pp. 585-591.
(Continued)

*Primary Examiner* — Kiet T Nguyen
(74) *Attorney, Agent, or Firm* — Kilpatrick Townsend & Stockton LLP

(57) ABSTRACT

Apparatus and methods for delivering biological samples to an ICP source of a mass cytometer are disclosed. Biological material is disposed on a plurality of discrete sites on a carrier. The plurality of discrete sites are configured to retain biological material and to release the biological material upon application of energy. The carrier is positioned in proximity to a gas conduit and upon release from the discrete sites, the biological material becomes entrained in a gas flow, which delivers discrete portions of biological material through the conduit to the ICP source for analysis by mass cytometry. The apparatus and methods can provide a continuous stream of discrete portions of biological material to a mass cytometer or mass spectrometer.

14 Claims, 10 Drawing Sheets

(51) Int. Cl.

| | |
|---|---|
| ***G01N 33/483*** | (2006.01) |
| ***H01J 49/00*** | (2006.01) |
| ***H01J 49/04*** | (2006.01) |
| *G01N 1/04* | (2006.01) |

(56) References Cited

U.S. PATENT DOCUMENTS

| | | | | |
|---|---|---|---|---|
| 7,671,330 | B2 | 3/2010 | Reilly et al. | |
| 8,879,064 | B2 * | 11/2014 | O'Connor | G01J 3/0291 356/432 |
| 9,261,503 | B2 | 2/2016 | Baranov | |
| 2008/0003616 | A1 | 1/2008 | Winnik et al. | |
| 2010/0144056 | A1 | 6/2010 | Winnik et al. | |
| 2010/0213367 | A1 * | 8/2010 | Miller | G01N 1/405 250/282 |
| 2012/0061561 | A1 | 3/2012 | Antonov et al. | |
| 2014/0121117 | A1 | 5/2014 | Tanner | |
| 2014/0287953 | A1 * | 9/2014 | Gunther | H01J 49/0463 506/9 |
| 2016/0071713 | A1 * | 3/2016 | Farmer, III | H01J 49/04 250/282 |

OTHER PUBLICATIONS

Doraiswamy et al., Excimer laser forward transfer of mammalian cells using a novel triazene absorbing layer, Applied Surface Science, vol. 252, Issue 13,, Apr. 30, 2006, pp. 4743-4747.

Fernández-Pradas et al., Laser-induced forward transfer of biomolecules, Thin Solid Films, vols. 453-454, Apr. 1, 2004, pp. 27-30.

Gao et al., Direct labeling microRNA with an electrocatalytic moiety and its application in ultrasensitive microRNA assays, Biosensor Bioelectronics vol. 22(6), Jan. 15, 2007, pp. 933-940.

Kyrkis et al., Direct Transfer and Microprinting of Functional Materials by Laser-Induced Forward Transfer, Chapter 7 in Recent Advances in Laser Processing of Materials, , Eds. Perriere et al. 2006, pp. 213-241.

Lee et al., Nanowire substrate-based laser scanning cytometry for quantitation of circulating tumor cells, Nano Lett., vol. 12(6), 2012, pp. 2697-2704.

International Application No. PCT/US2015/068330, International Search Report and Written Opinion dated Mar. 30, 2016, 13 pages.

Verboket et al., A New Microfluidics-Based Droplet Dispenser for ICPMS, Anal. Chem., vol. 86 (12), May 7, 2014, pp. 6012-6018.

Wang et al., Three-dimensional nanostructured substrates toward efficient capture of circulating tumor cells, Angew Chem Int Ed Engl. vol. 48(47), 2009, pp. 8970-8973.

* cited by examiner

FOCUSING A FIRST LASER SPOT ONTO A FILM SUPPORTING THE BIOLOGICAL SAMPLE TO HEAT THE FILM, WHEREIN HEATING OF THE FILM LIFTS THE BIOLOGICAL SAMPLE INTO A GAS PHASE WITHOUT COMPLETE VAPORIZATION OF THE BIOLOGICAL SAMPLE, THE GAS PHASE C

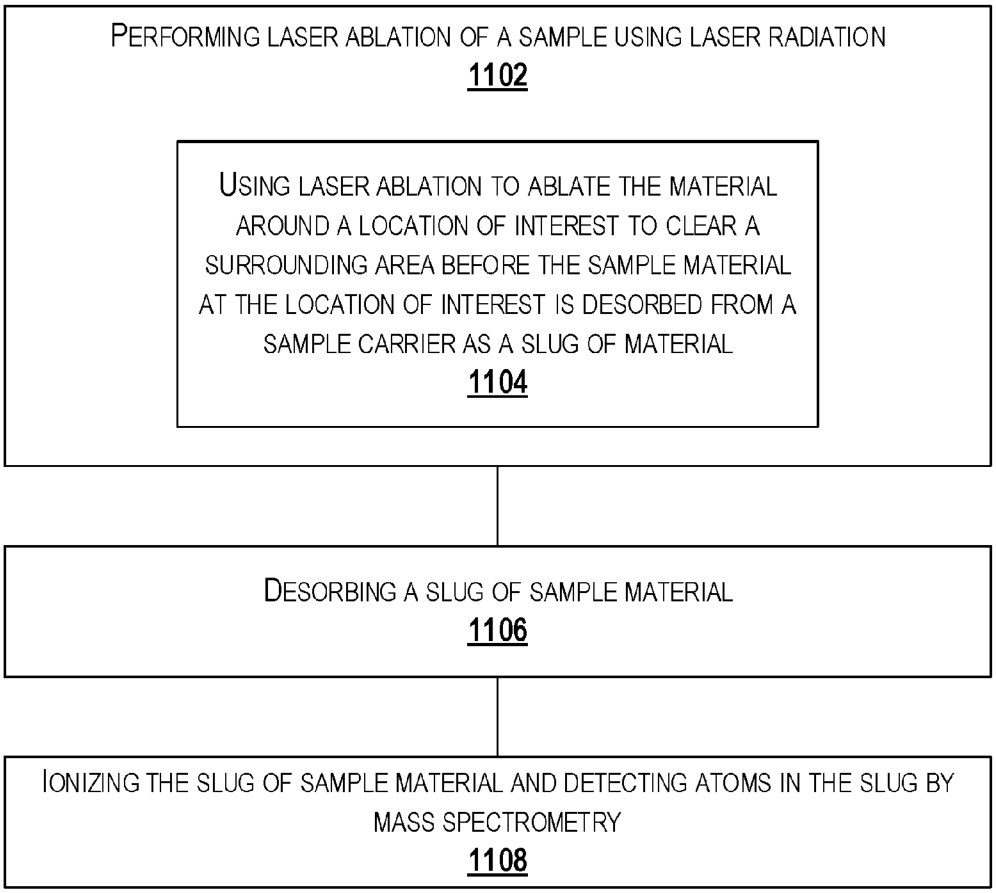

FIG. 11

PERFORMING LASER ABLATION OF A SAMPLE USING LASER RADIATION
1102

USING LASER ABLATION TO ABLATE THE MATERIAL AROUND A LOCATION OF INTEREST TO CLEAR A SURROUNDING AREA BEFORE THE SAMPLE MATERIAL AT THE LOCATION OF INTEREST IS DESORBED FROM A SAMPLE CARRIER AS A SLUG OF MATERIAL
1104

DESORBING A SLUG OF SAMPLE MATERIAL
1106

IONIZING THE SLUG OF SAMPLE MATERIAL AND DETECTING ATOMS IN THE SLUG BY MASS SPECTROMETRY
1108

STRUCTURED BIOLOGICAL SAMPLES FOR ANALYSIS BY MASS CYTOMETRY

CROSS REFERENCE TO RELATED APPLICATIONS

This application claims priority to and the benefit of U.S. Provisional Patent Application 62/108,911 filed Jan. 28, 2015 and U.S. Provisional Patent Application 62/098,890 filed Dec. 31, 2014, the contents of which are incorporated herein in their entirety.

FIELD

The present disclosure relates to apparatus and methods for introducing biological samples to a mass cytometer.

BACKGROUND

Mass cytometry is a newly developed technique for studying biological samples. The technique was originally developed to study cell populations in which samples of interest containing various biological cells were "stained" with affinity probes such as antibodies that are attached to elemental tags. The amount of affinity probes of a given type attached to each cell can be used to characterize each individual cell. The amount of affinity probe of each type is directly related to the amount of the associated elemental tag. The amount of the elemental tagging material can be measured by passing the cell through an inductively coupled plasma (ICP) ion source of a mass cytometer. The technique of "staining" biological material with affinity probes with elemental tags has recently been extended to the field of imaging of biological tissue. In imaging mass cytometry, a tissue of interest is "stained" with affinity probes/molecular tags and laser ablation can be used to extract the elemental tags from discrete locations (pixels) on the tissue. Imaging mass spectrometry follows a similar method, except that it relies on the detection of atoms naturally present in the sample rather than the labelling atoms in the elemental tags.

A limitation of mass cytometry is the efficiency of introducing biological samples such as cells into the mass cytometer. Cell introduction efficiency of commercial mass cytometers is about 30%. This means that more than two-thirds of biological cells in a sample are lost before they can be recorded by the mass cytometer.

A further limitation of laser-ablation based imaging mass cytometry and laser-ablation based imaging mass spectrometry is the low pixel recording rate. The pixel recording rate is limited by the washout time of the laser ablation cell and the connecting gas conduits. Even the fastest laser ablation cells have a washout time on the order of 30 ms. This is much slower than the intrinsic recording capabilities of the mass cytometer or mass spectrometer. In a typical mass cytometer cell throughput can be as high as 1000 cells per second; however, the spread of the laser ablation plume as it travels through the laser ablation apparatus, i.e. washout time, limits the pixel rate to about 30 pixels per second. Moreover, in the process of laser ablation each pixel of material is vaporized and converted into an aerosol. The aerosol plume is then transported to the ICP source via a gas conduit. One of the problems with this approach is that a fraction of the aerosol plume can contaminate neighboring areas, e.g., neighboring pixels, of the tissue sample. Some fraction of the aerosol plume can also be lost during transport through the gas conduit connecting the laser ablation chamber to the ICP ion source. In addition, the gas dynamic spreading of the aerosol plume during transport to the ICP source further limits the washout time. Therefore, in view of these constraints, it is desirable to avoid remote ablation method and aerosol plume formation of a biological sample and thereby improve the throughput of imaging mass cytometry and imaging mass spectrometry.

SUMMARY

An ionization source, for example an ICP source, is able to evaporate, dissociate, and ionize biological material introduced directly into the source and provide full elemental response to tagging components according to the standard function of the mass cytometer (or detection of atoms naturally present in the sample, by a mass spectrometer, if the sample is not labelled). In other words, an ionization source, for example an ICP source, of a mass cytometer is entirely capable of interrogating and ionizing biological material representing individual areas or pixels of a tissue. By creating a stream of individual pixels representing discrete areas of tissue or individual cells entrained in a suitable gas flow, each pixel can be analyzed by the mass cytometer or mass spectrometer. This approach has several advantages compared to methods involving introduction of aerosol plumes into an ionization source, for example an ICP source, of a mass cytometer or mass spectrometer.

Apparatuses and methods that facilitate introduction of biological material directly into an ionization source, for example an ICP source, of a mass cytometer are provided. Apparatuses and methods utilizing pre-structured, addressable, biological samples able to introduce discrete material pixels into a gas stream and subsequently into an ionization source, for example an ICP source, of a mass cytometer or mass spectrometer are disclosed.

In a first aspect, carriers are provided, comprising: a surface; a plurality of discrete sites disposed on the surface, wherein, each of the plurality of discrete sites is configured to retain a biological sample; and each of the plurality of discrete sites is configured to release the biological sample upon application of an energy impulse. In some embodiments, the carrier may include a sacrificial layer configured to be targeted by a laser. The sacrificial layer, when ablated by the laser, may eject biological material disposed on the sacrificial layer into a gas stream. In some embodiments, a cushion layer may be provided between the sacrificial layer and the biological material. The cushion layer may be configured to protect the biological material from the ablation of the sacrificial layer.

In a second aspect, systems for introducing biological samples into an ionization source, for example an ICP source, of a mass cytometer or mass spectrometer are provided, comprising: the carrier provided by the present disclosure; a conduit comprising an inlet and an outlet, wherein, the inlet is disposed in proximity to the surface of the carrier; and the outlet is disposed in proximity to an ionization source, for example an ICP source; a gas flow configured to entrain a biological sample released from a discrete site and to direct the released biological sample through the conduit to the ionization source, for example the ICP source.

In a third aspect, methods of preparing a structured biological sample are provided, comprising: providing the carrier provided by the present disclosure; flowing a solution comprising a plurality of discrete biological material over the surface of the carrier to cause the biological material to be retained by the plurality of discrete sites; removing excess solution to provide a structured biological sample comprising biological material retained on the plurality of discrete sites.

In a fourth aspect, methods of preparing a structured biological sample are provided, comprising: providing the carrier provided by the present disclosure, wherein, the surface comprises topographic features configured to cut a biological sample; and the topographic features are disposed between the plurality of discrete sites; and applying a biological sample onto the surface of the carrier to cause the topographic features to cut and section the biological sample, and to cause the sections of biological material to be retained by the plurality of discrete sites to provide a structured biological sample.

In a fifth aspect, methods of preparing a structured biological sample are provided, comprising: providing the carrier provided by the present disclosure, applying a biological sample to the surface of the carrier; and sectioning the biological sample to remove portions of the biological sample between the plurality of discrete sites to provide a structured biological sample.

In a sixth aspect, methods of delivering a biological sample into an ICP torch are provided, comprising: providing the carrier provided by the present disclosure, wherein the plurality of discrete sites comprises a biological sample; positioning one of the plurality of discrete sites in proximity to an inlet of a conduit, wherein the conduit comprises an outlet disposed in proximity to an ionization source, for example an ionization source, for example an ICP source, of a mass cytometer or mass spectrometer; providing a gas flow over the discrete site and through the conduit; releasing the biological sample from the discrete site; causing the released biological sample to become entrained by the gas flow, wherein the gas flow delivers the biological sample to an ionization source, for example an ICP source, of a mass cytometer or mass spectrometer; and positioning a second of the plurality of discrete sites in proximity to the inlet of the conduit.

In some aspects, a method of delivering a biological sample into a mass cytometry system may be provided. The method may include focusing a first laser spot onto a film supporting the biological sample to heat the film. The heating of the film may lift the biological sample into a gas phase without complete vaporization of the biological sample. The gas phase configured to deliver the biological sample to the mass cytometry system.

The film may be coupled with a substrate. The film may be a plurality of separate portions of film at discrete spaced apart sites on the substrate. The plurality of separate portions of film may define a plurality of cell capture sites. The cell capture sites may be configured to capture only a single cell. A surface of gaps between the plurality of separate portions of film may be modified to repel the biological sample.

Optionally, the first laser spot may be focused onto the film supporting the biological sample to ablate the film. A cushion layer may be disposed between the biological sample and the film. The cushion layer may be configured to absorb energy from the ablation of the film to limit damage to the biological sample from the ablation of the film. A surface of the cushion layer may be modified to preferentially capture a target biological sample.

In some embodiments, the method may include focusing a cutting laser spot onto the film to cut around the biological sample to separate the portion of the film supporting the biological sample from a bulk of the film. The cutting laser spot may be from a first laser, and the first laser spot may be from a second laser different from the first laser.

In some aspects of the present disclosure, a method of delivering a biological sample into a mass cytometry system may be provided that may include focusing a laser spot onto a film supporting the biological sample to ablate the film at a location adjacent to the biological sample. The ablation of the film at a location adjacent to the biological sample may lift the biological sample into a gas phase without complete vaporization of the biological sample. The gas phase may be configured to deliver the biological sample to the mass cytometry system. In some embodiments, the film may be ablated at a location that is no more than 5 microns from the biological sample.

BRIEF DESCRIPTION OF THE DRAWINGS

The drawings described below are for illustration purposes only and are not intended to limit the scope of this disclosure.

FIG. 11 is a flowchart depicting a method of analyzing a sample.

Reference is now made in detail to certain embodiments of devices, apparatus, and methods. The disclosed embodiments are not intended to be limiting of the claims. To the contrary, the claims are intended to cover all alternatives, modifications, and equivalents.

DETAILED DESCRIPTION

Structured biological material is used to introduce discrete samples or pixels of biological material into an ionization source, for example an ICP source, of a mass cytometer or mass spectrometer. Structured biological material refers to material such as individual cells, tissue portions, or other aggregation of biological material, arranged in discrete, addressable sites on a carrier. The structured biological material can be released from the carrier and each discrete material pixel sequentially introduced into a mass cytometer or mass spectrometer for analysis. Benefits of sequential introduction of discrete material pixels as opposed to random introduction of biological samples as in conventional mass cytometry or mass spectrometry include a higher sample processing rate and elimination of multimers such as dimers, trimers, etc., caused by the simultaneous arrival of multiple entities. By eliminating multimers the processing and analysis of the data can also be simplified.

A "pixel" refers to a portion of a material sample that is introduced at an instant in time into an ionization source, for example an ICP source, of a mass cytometer or mass spectrometer. In certain embodiments, a pixel represents a cell or group of cells, and in certain embodiments, a portion of a tissue section or other discrete biological sample. A pixel may have any suitable dimension or shape. For example, a pixel can have dimensions from 10 nm to 10 μm, from 100 nm to 10 μm, and in certain embodiments from 1 μm to 100 μm. The terms "pixel" and "discrete site" are used interchangeably. The material from a pixel is not vaporized during release from a carrier or during transit to an ionization source, for example an ICP source.

Figure 1:
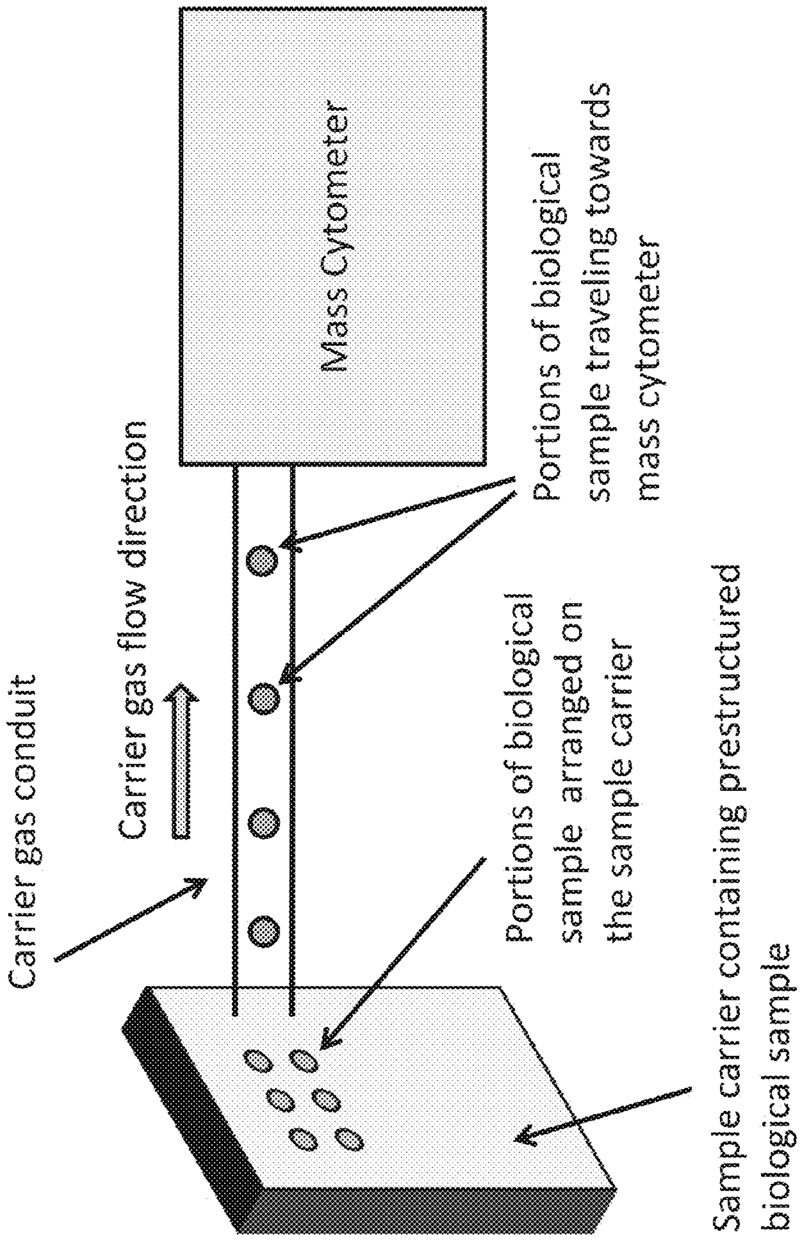
FIG. 1 shows a schematic diagram of generic description of a mass cytometer instrument configuration operating with pre-structured samples according to certain embodiments.

FIG. 1 shows a schematic diagram of a mass cytometry instrument operating with a structured sample. A sample carrier having discrete sites or pixels containing biological material serves as the source of biological material. The biological material can be individually lifted from the discrete sites to become entrained in a carrier gas flow. The carrier gas flow maintains the separation of the discrete biological material to inject the discrete biological material into an ionization source, for example an ICP source, where the biological material is vaporized and ionized and subsequently analyzed by mass spectrometry.

In certain embodiments, the surface of the carrier configured with discrete sites is mounted perpendicular to or substantially perpendicular to a carrier gas conduit. The inlet of the carrier gas conduit can be situated in close proximity to the surface of the carrier. Carrier gas flowing into the gas carrier conduit can enter through the inlet and/or other apertures near to or included with the conduit. The conduit inlet may contain one or more skimmers or conical shaped elements to facilitate capture of a desorbed biological sample and/or direct desorbed sample into the gas conduit. Sometimes, the surface of the carrier does not have discrete sites. Here, particular methods of ablation and desorption, such as those discussed below, can be used to analyze particular portions, such as cells or groups of cells, of the biological sample without partitioning of the sample into discrete parts of the sample at discrete sites.

Various apparatus and methods for introducing an ablated plume of material into a carrier gas stream for introduction into an ionization source, for example an ICP source, are disclosed in International Application No. WO 2014/169394, which is incorporated by reference in its entirety. Similar apparatus and methods can be employed with embodiments provided by the present disclosure for introducing a non-vaporized sample of biological material into the carrier gas flow. The various embodiments show a carrier gas stream flowing across the surface of the target, directed gas flows, skimmers, and gas conduits disposed anywhere from perpendicular to horizontal with respect to the carrier surface.

The carrier may be mounted on a translation stage. The translation stage may be capable of moving the surface of the carrier toward and away from the inlet to the gas conduit. The translation stage may also be configured to move the carrier in directions perpendicular to the carrier gas conduit. The translation stage is configured to move the carrier with respect to the inlet of the gas conduit from site to site at a rapid rate. By moving the carrier from site to site and desorbing a biological sample at each site, a stream of discrete packets of biological material may be introduced into the carrier gas and transported to an ionization source, for example an ICP source, of a mass cytometer.

Sample Carrier

The invention provides a carrier comprising: a surface; a plurality of discrete sites disposed on the surface, wherein each of the plurality of discrete sites is configured to retain a biological sample; and each of the plurality of discrete sites is configured to release the biological sample upon application of an energy pulse.

The invention also provides a carrier comprising: a surface, wherein the surface is configured to retain a biological sample and the surface is configured to release the biological sample upon application of an energy pulse. The kinds of energy that can cause the release of the biological sample (i.e. desorption) from the sample carrier are discussed further below.

In some embodiments, each of the plurality of discrete sites is characterized by an area from 1 μm to 100 μm in circumscribed diameter. In some embodiments, the plurality of discrete sites comprises affinity molecules configured to retain the biological sample.

In some embodiments, the carrier comprises a channel underlying the plurality of discrete sites, wherein the channel extends through a thickness of the carrier; and the plurality of discrete sites comprises a hole fluidly coupled to the channel.

In some embodiments, the plurality of discrete sites is individually addressable.

As discussed in more detail below in some embodiments, the plurality of discrete sites comprises a thermally desorbable material configured to release the biological sample. Likewise, discussed in more detail below, the sample can be desorbed from the sample by thermal energy, mechanical energy, kinetic energy, and a combination of any of the foregoing. One example is the use of laser radiation energy, in a technique called lifting (laser induced forward transfer; see e.g. Doraiswamy et al., 2006, Applied Surface Science, 52: 4743-4747; Fernández-Pradas, 2004, Thin Solid Films 453-454: 27-30; Kyrkis et al., in Recent Advances in Laser Processing of Materials, Eds. Perriere et al., 2006, Elsivier). Accordingly, in some embodiments, the sample carrier comprises a desorption film layer. In other words, the sample carrier has a film layer on the surface of the carrier which is for receiving the sample, and which assists the separation of the sample from the sample carrier by absorbing laser radiation. The desorption film can absorb the radiation to cause release of the desorption film and/or the biological sample (e.g. in some instances the sample film desorbs from the sample carrier together with the biological sample, in other instances, the film remains attached to the sample carrier, and the biological sample desorbs from the desorption film).

In certain embodiments, a sample carrier includes a cover with a window. A cover can protect the biological samples prior to desorption and/or can facilitate control of carrier gas flow over the sample. The carrier can be moved with respect to a window so as to bring the discrete samples on the carrier surface under the window. The window can have features that facilitate capture of a biological sample by the gas conduit such as carrier gas channeling and/or electrostatic features. For example, in certain embodiments it is desirable that the carrier gas flow be laminar to facilitate the ability to systematically introduce pixels of biological sample into the gas flow and subsequently into the ionization source, for example an ICP torch. Use of a cover with a window can help to maintain consistent sample-to-sample gas dynamics to facilitate entrainment of discrete biological material pixels into the gas stream.

In certain embodiments, the sample carrier is in the form of a plate. The plate may have a substantially flat surface or other suitable surface topography. In some embodiments, the carrier comprises a topographically defined surface configured to retain the biological sample. For example, in certain embodiments, the plate may have recessed features for retaining biological sample and/or raised features for retaining biological sample. The surface of a plate may have channels or other suitable features for controlling gas and/or liquid flow containing samples across the surface of the plate and/or for facilitating entrainment of desorbed biological sample into the carrier gas flow. For example, posts may be provided with capture sites. The post geometry may be configured to aid in gas dynamics by allowing the flow of the carrier gas to envelope the material being lifted.

In certain embodiments, such as when the biological sample is a tissue section, the sample carrier may be characterized by corrugated surface features having raised edges configured to cut and separate an applied tissue section. As a tissue section is applied to a carrier surface having features with cutting edges the tissue section can be separated into individual regions or pixels that become physically separated from each other.

Discrete capture sites may have a suitable area as appropriate for capturing a particular biological material. For example, eukaryotic animal cells have dimensions from about 10 μm to about 30 μm. A discrete capture site can include properties that facilitate the capture and/or retention of a biological material on the discrete site. The property may be chemical in nature such as an affinity molecule or other chemical interaction that facilitates adsorption or adhesion. The property may be electrostatic, and in certain embodiments, the property may be physical such as having surface features that facilitate adhesion, which can include roughened or specially designed adhesion surface such as having spiny or hooked features.

In certain embodiments, a discrete site may have a multilayer structure with layers designed for different purposes. For example, an exterior or top layer may be configured to capture and retain a biological sample, an interior layer may be configured to heat the discrete site to desorb or release the biological material from the discrete site, and a lower layer may be configured for adhesion to the substrate material. In some embodiments, the top layer may provide the capture site properties that facilitate the capture of targeted biological material. For example, the top layer may provide the preferential chemical binding with the biological material (e.g., through affinity molecules or the like). The top layer may also provide the electrostatic forces for attracting biological material in some embodiments and/or the surface features (e.g., roughened surface features, hooks, and/or spines or the like).

In certain embodiments, a carrier may have other geometries. The functions of the carrier may include capturing a biological sample, retaining a biological sample, and/or facilitating selective release of the biological sample from the surface of the substrate. Thus, although planar substrates or plates may be used, other structures such as beads, filaments, tubes, rods, meshes, and other suitable supporting structures may be employed as carriers. As appropriate for a particular carrier geometry, an associated structure may also be used to control gas flow over the surface of the carrier. For example, in certain embodiments a carrier may comprise a filament or rod within a surrounding tube. The filament serves as a support and the surrounding tube channels gas flow for entraining the desorbed biological sample and for introduction into the ionization source, for example an ICP torch.

Biological Samples

In certain embodiments, a biological sample is a cell and in certain embodiments, a tissue section.

In certain embodiments, a discrete capture site contains a single cell or multiple cells.

In certain embodiments, a biological sample can be a virus, a bacteria, a subcellular structure such as a nucleus or mitochondrion, or a eukaryotic plant cell.

Sample Capture

In certain embodiments, sample capture and release can be a dynamic process meaning that the capture and release processes occur more or less (e.g., nearly) simultaneously. For example, a biological sample such as an isolated cell may be introduced into a fluid, which flows over the surface of a carrier. As the fluid with entrained sample flows over discrete sites, the sample becomes captured at the discrete sites. Once a sample is captured, a desorption or lifting process may be activated to eject the sample (e.g., a cell or the like). In some embodiments, a sample capture detector may be provided that may be operatively coupled with the desorption or lifting mechanism (e.g., laser, bubble-jet type mechanism) to release the captured sample into the gas phase. The capture detector can, for example, be based on forward or side scattering information from the cell that is captured. Or, it can be based on detection of a fluorescent signal from a cell that is stained with a particular reagent to produce the fluorescent signal. In addition, the appearance of the cell can be detected by a CCD camera using a microscope style observation of the capture site in some embodiments. Other—not optical methods can be employed, such as probing of solution for electrical conductivity—similar to the Coulter method or probing solution with high frequency electrical signals. Accordingly, in some embodiments, some sites may be capturing samples while other sites are releasing samples.

Optionally, a timing controller may be provided that is operatively coupled with the sample capture detectors and the desorption or lifting mechanism. The timing controller may delay a release event when a cell capture is detected until the start of the next time window in the data acquisition setup. Accordingly, such a setup and method may convert a random arrival of cells in a flow to an equally spaced in time release events in the gas phase. This approach may reduce or otherwise eliminate "doublet" and other "multiplets" commonly detected in mass cytometry when the system is operating in solution mode due to the randomness of cell arrival.

In certain embodiments, the carrier may be externally loaded with biological sample, where the cells are fixed to the carrier prior to the introduction of the sample carrier into the cell lifting chamber. Biological sample may be loaded passively or actively. For example, when loaded passively a solution containing biological sample may be applied over the surface of the carrier and the biological sample allowed to affix to discrete sites on the carrier surface. With an actively loaded sample a biological material may be deposited at a discrete site. The discrete sites can have patches of binding media such that the cells will adhere only at the discrete sites. Thus, instead of the randomly scattered cells on the slide, the cells may be arranged on the capture sites, and optionally, the capture sites can be spaced at regular intervals to facilitate more convenient targeting for the laser. In some embodiments, the capture sites are configured or sized to hold only one cell per site.

Discrete sites may include an affinity moiety for binding to complementary sites of a biological sample and/or may be characterized by other properties or chemical functionality suitable for capturing generic or specific biological sample. For example, a capture site can include molecules that enhance ionic or hydrophobic-hydrophilic interactions with the biological material.

Figure 2:
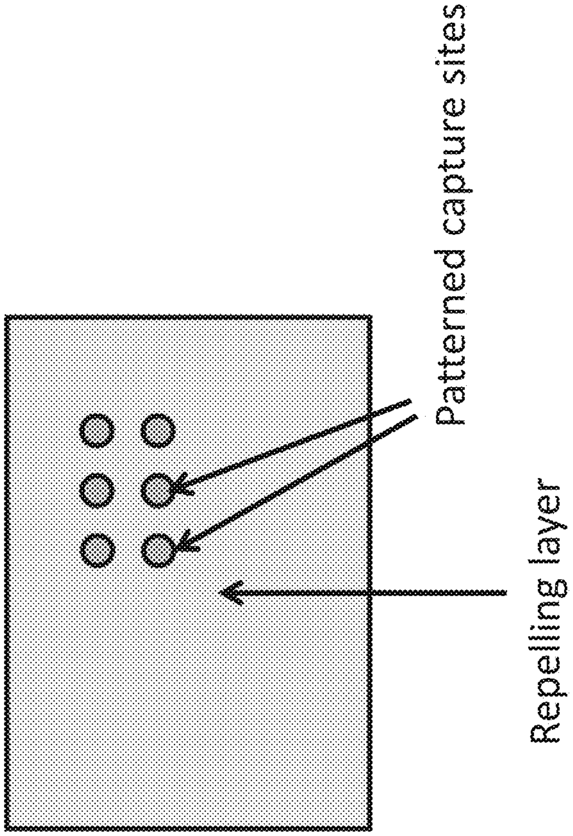
FIG. 2 shows an example of patterned capture sites on a sample carrier.

In certain embodiments, the region of a carrier surface not containing capture sites may be covered with a material that cells will not adhere to and/or that causes biological material to aggregate at the discrete capture sites. An example is shown in FIG. 2 in which a "repelling" layer of material is disposed on the carrier surface not covered by the discrete capture sites.

An example of one approach to capturing cells is disclosed by Wang et al. in which an antibody-coated (anti-EpCAM-coated) three-dimensional nanostructured substrate that provides enhanced capture of EpCAM-positive cells from a cell suspension. Wang et al., *Angew. Chem. Int. Ed. Engl.* 2009, 48(47), 8970-8973). The interdigitation of nanoscale cellular surface components and the silicon-nano-pillar array enhances local topographic interactions resulting in improved cell-capture efficiency. Other suitable apparatus and methods for capturing cells are described in Lee et al., Nano. Lett. 2012, 12(6), 2697-2704. In some embodiments, the capture sites are configured to capture one cell per site such that single cell analysis may be performed using mass spectrometry or mass cytometry. Optionally, in some embodiments, the capture sites may include one or more immobilized antibodies which bind to a cell surface marker of the cell(s) of interest.

Figure 3:
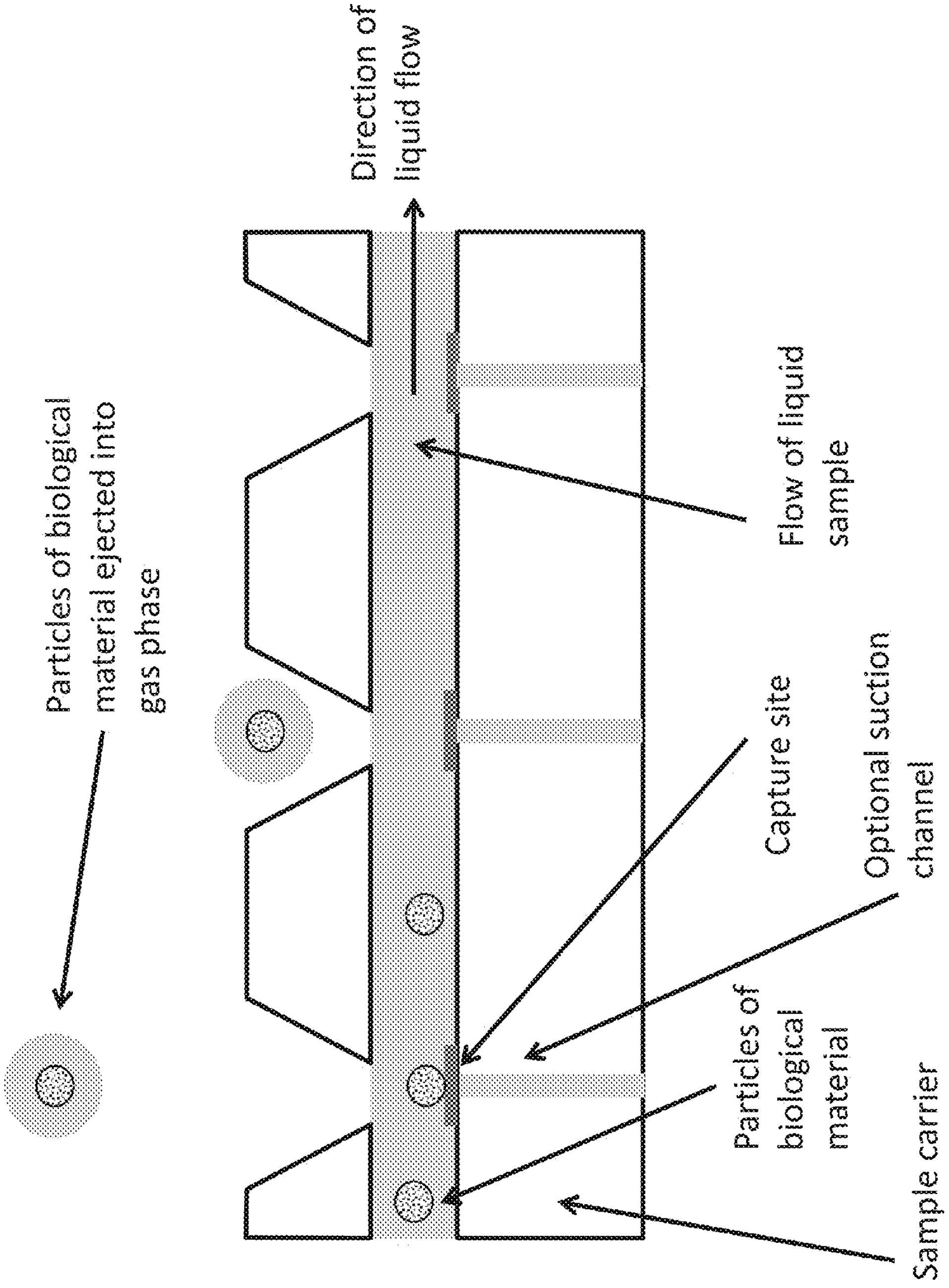
FIG. 3 shows a liquid interface and sample carrier with patterned capture sites on a sample carrier for introducing discrete biological samples into a gas stream according to certain embodiments.

Mechanical methods may also be used to capture cells. FIG. 3 shows an example of a carrier having patterned captured sites with each capture site coupled to a channel extending through the thickness of the carrier. Each capture site includes one or more small holes. A solution containing biological material such as cells is flowed over the surface of the carrier and when suction is applied to a channel passing cells can be pulled onto a capture site and retained. To release the biological material from a capture site, pressure can be applied to the channel to eject particles of biological material through the solution flow and into a gas stream for injection into an ionization source, for example an ICP source. As shown in FIG. 3, the biological material can include a certain amount of liquid when ejected into the gas phase. The pressure surge can be created by a piezo actuator or by a pulsed heater that creates a bubble-jet effect or by a pressure spike created by absorption of laser radiation near the biological material The stream of gas phase particles of biological material somewhat resemble a stream from a drop on demand (DoD) droplet generator. As DoD generators are known to operate with an ionization source, for example an ICP ion source, the steam of particles produced by this embodiment could also be made compatible with the ionization source, for example the ICP ion source. A potential benefit of this arrangement over a DoD generator is that the capture sites can be designed to retain only one particle of biological material such as a cell. Captured biological material can be released at equally spaced time intervals and thereby minimize confusion caused by the overlap of signal transients from each particle, which is a common problem when cells are entering an ionization source, for example an ICP source, at random. The capture function of the capture site can be facilitated by simple mechanical means such as obstructions in the flow or by an optional vacuum suction channel in which some liquid is pulled down as a cell is stopped by the diameter restriction at the capture site. Once a particle is captured it can then be ejected into the gas flow using suitable means such as by explosive evaporation caused by a laser pulse directed at the capture site or by explosive evaporation caused by individually addressable microheaters arranged under each of the capture targets. Particles of biological material can also be ejected by an application of a strong electric field. Appropriate electrode arrangements can be incorporated on or around the capture sites for applying strong electric fields and causing ejection of captured material. The droplets can be also be ejected using microelectromechanical systems—(MEMS) based microactuators. An array of MEMS micro-mirrors as used in commercial digital projection chips represents an example of densely packed fast moving microactuators.

In certain embodiments, pre-structuring biological tissue in only one dimension can take place on a thin ribbon or tape. The ribbon can be the arranged in a spool. The spool can be arranged in such a way that each turn of the ribbon is separated from the next turn by a gap to avoid smearing the sample. The ribbon can contain capture spots for sample pre-structuring. The sample can be recorded on the spool by bringing liquid sample through a capillary in contact with the moving ribbon as the ribbon is wound on the spool. The liquid can be allowed to dry while the captured biological material will stay attached to the capture sites.

In certain embodiments, the carrier support is not structured and the biological samples are irregularly distributed on the surface of the carrier. For example, a solution of biological material such as cells can be applied to a support. The cells can adhere randomly to the support. Using microscopy, the position of each of the deposited cells can be determined and mapped. The carrier can be translated into a position proximate a gas conduit according to the mapped position of the cells and the cells released into a carrier gas flow. The cells can be selected based on functional imaging, separation from adjacent cells, and/or other criteria. U.S. patent application Ser. No. 14/060,125, the contents of which are incorporated herein by reference, describes methods and systems for interrogating a sample for identifying locations of target cells for location specific ablation that may be used with embodiments described herein. Alternatively, the sample on a non-structured carrier may be a tissue section, and similarly, regions of interest can be identified, for example by microscopy. The regions of interest can be desorbed using techniques discussed herein, such as controlled heating at the region of interest, or by lifting (such as when the sample carrier comprises a desorption film layer).

Tissue

In certain embodiments, the biological material is a biological tissue such as a biopsy section. In these applications, one of the functions of the carrier is to separate the tissue into discrete areas and retain the areas prior to release. When retained by the carrier the tissue can be separated into discrete areas having dimensions, for example, of 1 μm, 2 μm, 3 μm, 4, μm, 5 μm, 6 μm, 7 μm, 8 μm, 9 μm, 10 μm, or other suitable dimension.

Figure 4:
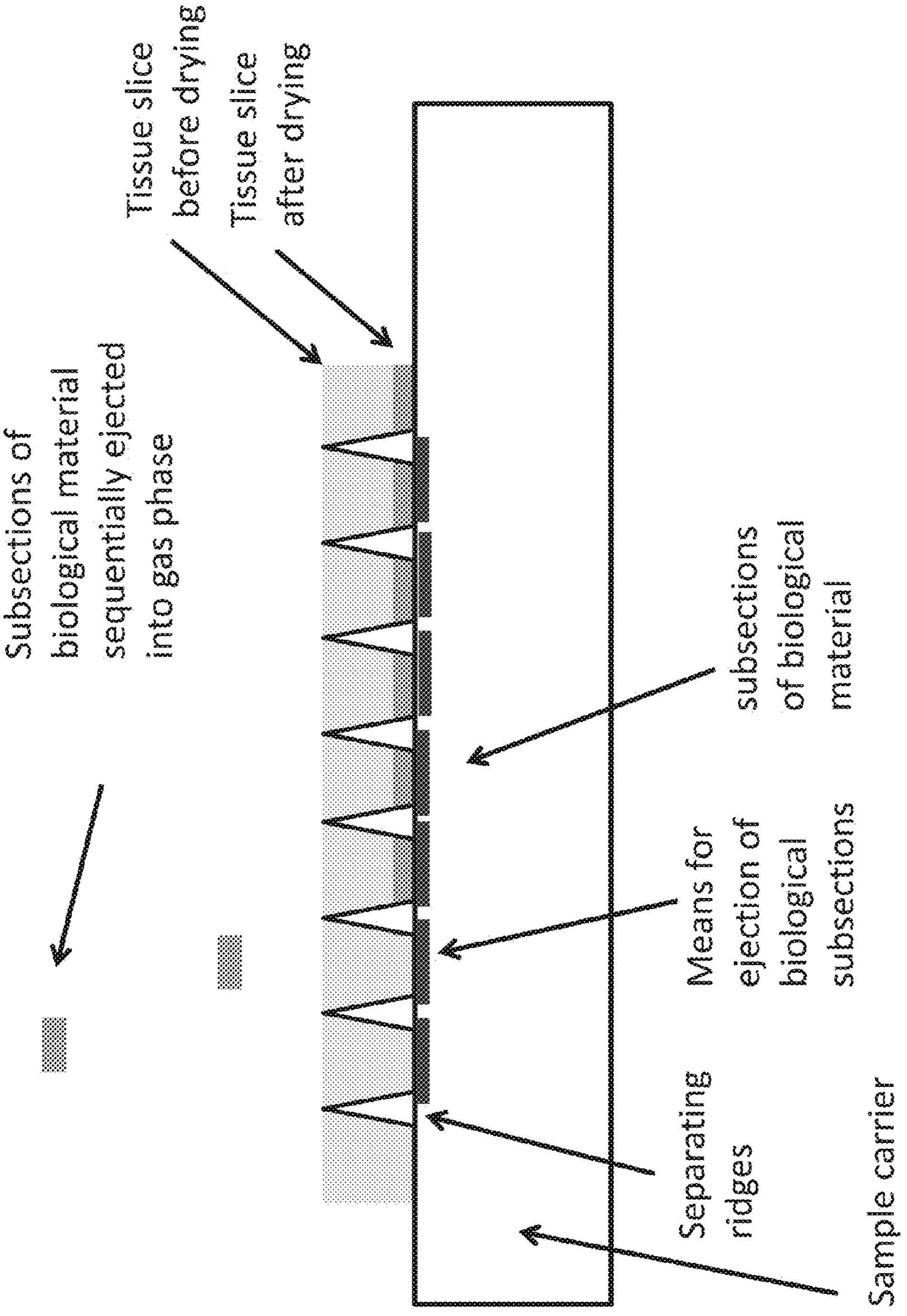
FIG. 4 shows an example of a structured tissue sample for imaging application and associated carrier according to certain embodiments.

The tissue can be separated by means of ridges having cutting edges that separate the tissue when the tissue is mounted on the surface of the carrier. An example of a carrier with serrated cutting edges between discrete capture sites is shown in FIG. 4. As shown in FIG. 4, a wet tissue slice is applied over a structured carrier. During application the knife edges of surface features cut and separate the biological tissue, which further shrinks and separates during drying. The sectioned sample rests on discrete sites of the sample carrier, which are configured to facilitate release of the biological material from the carrier. In certain embodiments, a wet tissue sample can be thicker than the height of the walls separating adjacent areas, and the walls are slightly higher or about the same height above the carrier surface as the dried tissue slice.

Alternatively, a tissue may be mounted on the surface of a carrier having discrete capture sites and divided into discrete areas by cutting the tissue into sections using, for example, a mechanical, electrical, or laser scribe.

Figure 5:
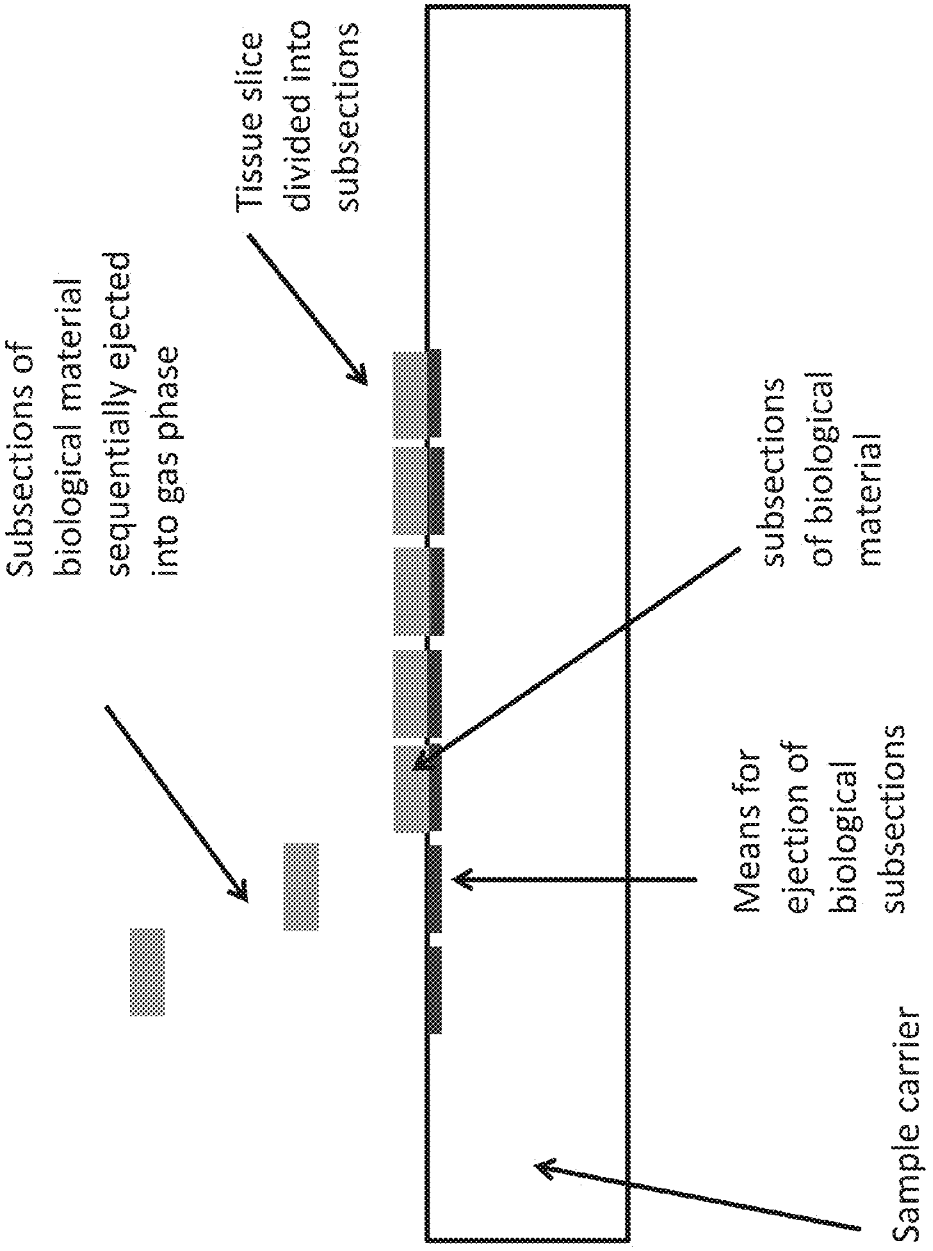
FIG. 5 shows an example of a pre-structured tissue sample with gaps between subsections for imaging applications and associated carrier according to certain embodiments.

In certain embodiments, the substrate ridges can act to minimize the spillover of radiation used for sample desorption on the neighboring discrete sites or pixels. Because the dimensions of the ridges can be on the scale of a wavelength of light, and because the light energy boundary is smeared on the scale of the wavelength the ridges that have a scale of the wavelength of light can play an important role in preventing the light from irradiating neighboring pixels. FIG. 5 shows another embodiment for tissue imaging applications. As shown in FIG. 5 the tissue under investigation is first sectioned into individual subsections on the sample carrier. The subsections are then sequentially ejected into the gas phase for further analysis. Each subsection can be separated from the remaining tissue using a variety of tools. Sub-sectioning can be used to ensure that when one subsection is launched into the gas phase other subsections are not dragged with it. The interface between the tissue sample and the sample carrier can include an adhesive layer to further improve the ability of other subsections to remain on the sample carrier. The adhesive layer can also have the properties of the light absorbing material suitable for a particular wavelength.

The sectioning of each subsection from the tissue can be accomplished by mechanical tools such as blades or stamps. Alternatively, the material between subsections can be removed by laser ablation in a separate sample preparation setup. In certain embodiments, the material can be removed by a setup employing a focused electron or ion beam. The focused electron or ion beam can lead to particularly narrow cuts (potentially on the 10 nm scale) between subsections leading to a pixel size on the order of 1 μm or in certain embodiments, 100 nm.

Other embodiments include combining the functions of the sectioning setup in the same chamber as the ejection setup. For example, the system can include one laser providing light on the samples shaped to cut gaps between subsections by interacting and desorbing tissue material in the gaps, and then a second laser can be used to interact with light absorbing material under each subsection to launch the pixel of biological material into the gas phase. The benefit of such designs is in the sharing of a large portion of the optical path. Optionally, a cushion layer may be provided between the biological material and the light absorbing/sacrificial material. The cushion layer may be provided to protect the biological material during ablation of the light absorbing/sacrificial layer.

As shown in the figures the structuring of the carrier into discrete sites is often periodic in nature. However, in certain applications in may be desirable to focus analysis on one or more specific areas of a tissue or a cell smear or to target individual cells from a cell sample applied as a thin layer. Moreover, a user may also want to obtain an optical or other image of the tissue or a cell smear or the cells spreads over the carrier prior to the analysis by imaging mass cytometry or imaging mass spectrometry, in order, for example, to correlate the mass cytometry or mass spectrometry results with cellular or morphological structure. Also, by taking the optical image one will be able to record an image over a large area quickly and then identify the areas of interest that require in-depth characterization by imaging mass cytometry or imaging mass spectrometry. Using such methods sampling of the pixels or discrete sites will not necessarily be in a regular periodic pattern but will be detailed in certain areas.

To implement strategic sample analysis, the sectioned tissue sample can be first imaged and mapped. The mapping can represent a visual analysis. Alternatively, the mapping can be based on a distribution of a staining material, which may or may not be the same staining material as used for mass cytometry analysis. For example, the staining material may be a fluorophore. Alternatively, the staining material may be an element tag, which is imaged using, for example, radiography. The regions of interest for more detailed analysis using mass cytometry or mass spectrometry can be selected based on the mapping.

Another arrangement for imaging applications involves cutting a two dimensional sample into narrow strips (first step of pre-structuring) and then feeding the strips to a device that further cuts the strip into subsections (second step of pre-structuring) and transferring these subsections into the gas phase for analysis by mass cytometer or mass spectrometer. In certain embodiments, cutting a tissue sample into subsections involves laser cutting or mechanical cutting. In certain embodiments it is desirable to make mechanical cuts by operating a rotating cutting wheel with multiple cutting zones along the circumference. For instance, a cutting wheel can rotate at a rotational speed of 50 revolutions per second (3000 rpm) and if the wheel itself has 20 equally spaced cutting sites the rate of sub-sectioning the strip will be 1000 subsections (pixels) per second, which is a rate that matches the analysis throughput of a mass cytometer or mass spectrometer.

In some embodiments, a sample carrier can stretch after subsections have been precut. This can allow one to avoid the limitation of minimal pixel dimension imposed by the diffraction of light in systems that utilize focused laser beams for pixel ejection. Precutting with an ion beam or an electron beam can provide spatial resolution well below one micrometer enabling imaging analysis on a sub-micrometer scale. Folded biological material can be used to provide the stretching function. This approach can be particularly straightforward in the case of a linear (virtually one-dimensional) sample carrier. A ribbon can be folded to form an initial sample carrier. The biological sample can then be adhered to the top side of the folded ribbon and then precut at the junctions of each fold. After that the ribbon can be unfolded to provide a pre-structured biological sample with each sample pixel separated in space by a significant distance determined by the length of each folding step.

In operation, it is not necessary to avoid a complete overlap of the signals produced at the detector by material from adjacent pixels. For example, it can be desirable to operate the instrument with a higher pixel ejection rate such that the order of ejection of pixel subsections becomes mixed during transport into the gas phase. If this operation results in only a few out of a sequence pixels then software algorithms can be used to restore the correct order based on interpolation to the rest of the image. As can be appreciated, the apparatus and methods are suitable for use in imaging cytometry applications. Previously disclosed methods using laser ablation of a tissue cross-section can be time consuming and as disclosed herein the rate of sample introduction can be limited by spread of the aerosol plasma. In methods provided by the present disclosure, a tissue sample can be prepared on the structured carrier and stored for later imaging mass cytometry or imaging mass spectrometry analysis. Also, prior to IMC analysis, the sample may be assessed using optical, fluorescence, or other microscopy to identify specific areas of interest for subsequent IMC analysis.

Sample Desorption

In certain embodiments, the sample carrier is not moved with respect to other elements of the sample introduction apparatus such as with respect to a desorption source or the gas flow. Mechanical movement of the sample carrier such as with a translation stage can reduce the rate at which individual pixels can be generated and thereby reduce system throughout. As discussed below, desorption can be achieved by a variety of techniques, including lifting.

The terms desorb and desorption are generally used to refer to release of a biological sample for discrete sites on a carrier surface, without substantial vaporization (e.g., a majority of the sample not being vaporized). The terms include any suitable method such as thermal, photolytic, chemical, or physical. Desorb and desorption are distinguished from ablation and other processes in which a sample of biological material is substantially vaporized at the time it is released from a substrate.

In certain embodiments, a biological sample may be released from the sample by thermal mechanisms. In such embodiments, the surface of the discrete site becomes sufficiently hot to desorb the biological material. Heat can be provided by a radiative source such as a laser. The energy applied to the surface is sufficient to desorb the biological material, preferably without altering the biological sample. Any suitable radiation wavelength can be used, which can depend in part on the absorptive properties of a surface. In certain embodiments, a surface or layer of a discrete site may be coated with or include an absorber that absorbs incident radiation for conversion to heat. The radiation may be delivered to a top surface of a discrete site or to a bottom surface of a discrete site through the thickness of the carrier. The heated surface may be a surface layer or may be an inner layer of a multilayer structure of a discrete site. Desorption by heating can take place on a nanosecond time scale. Also, vaporization of the support layer can occur on a picosecond time scale when a picosecond laser pulses are used.

In certain embodiments, a discrete site can include a layer of an electrical conductor that heats up upon the application of a current. In such cases discrete sites are electrically connected to electrodes and the discrete sites are individually addressable.

In certain embodiments, a biological sample may be attached to a discrete site with a cleavable photoreactive moiety. Upon irradiating the cleavable photoreactive moiety with a suitable light source, the photoreactive moiety can cleave to release the biological sample.

In certain embodiments, a discrete site may include a coating or layer of a chemically reactive species that imparts kinetic energy to the biological sample to release the sample from the surface. For example, a chemically reactive species may release a gas such as, for example, $H_2$, $CO_2$, $N_2$ or hydrochlorofluorocarbons. Examples of such compounds include blowing and foaming agents, which release gas upon heating. Generation of gas can be used to impart kinetic energy to a desorbing biological sample that can improve the reproducibility and direction of release of biological samples from the discrete sites.

In certain embodiments, a discrete site may have photoinitiated chemical reactants that undergo an exothermic reaction to generate heat for desorbing a biological material.

In certain embodiments, the discrete sites may be mounted and/or coupled to MEMS devices configured to facilitate release of a biological material from the discrete sites on a carrier.

Optionally, a laser may be focused at a location adjacent to the sample being lifted, rather than at the sample location. For example, the laser may be focused on the order of a few micrometers adjacent to the sample being lifted. Lifting ablation will be quite violent (as all ablations are) but by separating the ablation from the cell, the lifting may be gentler. Put in another way, the separation of the laser ablation location from the sample location of a few microns (e.g., less than 10 microns, less than 5 microns, less than 3 microns, or the like) provides a cushion and the acting media that lifts the cell may be a compression wave generated by the nearby ablation. The ablation of material adjacent the sample may lift the sample from the supporting surface and into the gas phase.

In some embodiments, the sample may be supported by a portion of a support film. The film may be attached to the substrate. A laser may be focused around the edge of the biological sample to separate the portion of the support film from a remainder of the support film. Thereafter, the portion of the support film supporting the sample may be gently heated (e.g., using the same or a different laser) to lift the sample into the gas phase. This two-step cutting and separation approach may reduce the amount of energy required to lift the cell and may make the lifting less violent to reduce the chances of damaging the cell during lifting. For example, in some embodiments, an IR laser may be used to cut around an area of interest while a UV laser may be used to nudge the cell and the film off the substrate (if a substrate is used—sometimes the sample may just reside on the film).

This may be advantageous when the sample is irregularly or randomly captured. In some embodiments, the analysis systems may include laser steering components to steer the focal point relative to the sample in order to separate the portion of the support film from a remainder of the film. Additionally, as discussed above, the cells can be selected based on imaging techniques and/or other criteria. For example, U.S. patent application Ser. No. 14/060,125 describes methods and systems for interrogating a sample (e.g., fluorescence microscopy) to identify locations of target cells for location specific analysis that may be used with embodiments described herein. Such methods and systems may be particularly advantageous when the biological material has an irregular or random arrangement on the sample support.

Single cell analysis by mass cytometry is limited by the introduction rate and is currently much less than in fluorescent flow cytometry systems. Fluorescent flow cytometers are capable of analyzing around 30,000 cells/sec compared to about 1,000 cells/sec for current mass cytometers. Limitations associated with spread of the aerosol plume of the biological sample in the laser ablation chamber and during transport to the ionization source, for example an ICP source, further limits the ability to isolate discrete samples of biological material. Methods have been developed for introducing biological material such as droplets containing individual cells directly into an ionization source, for example an ICP source, using microfluidics. Verboket et al., Anal. Chem. 2014, 86, 6012-6018. However, such methods appear to be limited to sample introduction rates around 300 cells/sec and these methods do not prevent cases when multiple cells aggregate in one droplet.

Using apparatus and methods provided by the present disclosure it is anticipated that sample introduction rates from 1,000 cells/sec to 5,000 cells/sec are possible with the advantage of predictability of timing of cell arrival as well as removal of the instances when multiple cells are arriving simultaneously.

Figure 6:
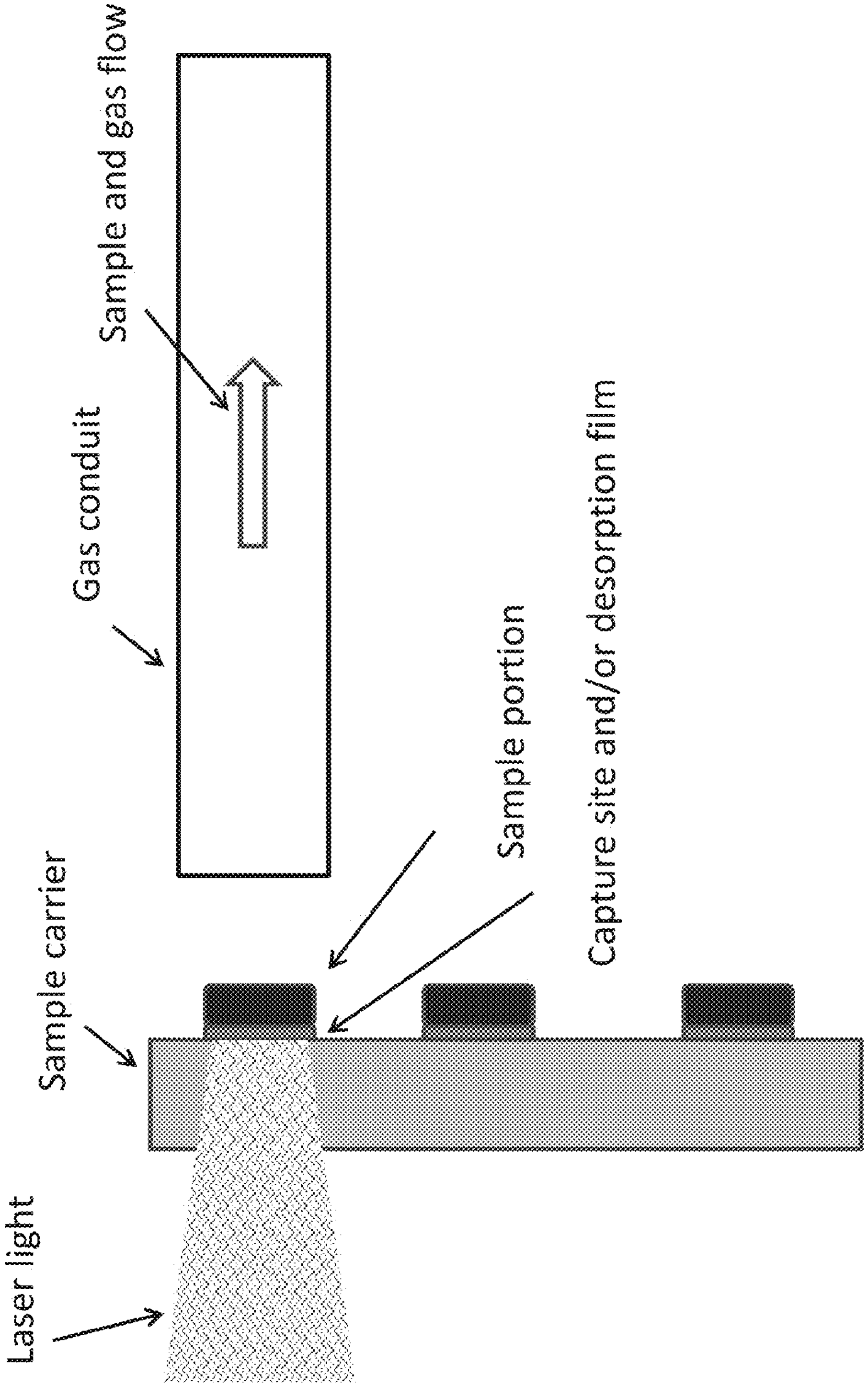
FIG. 6 shows a structured biological sample and associated carrier configured for laser desorption according to certain embodiments. The properties of light are chosen so that the carrier is virtually transparent while the desorption film at the capture site adsorbs the light and causes launching of the sample portion

FIG. 6 shows an example of a sample carrier with discrete sample sites disposed on a surface of the carrier. Each of the sample sites includes a capture layer and a desorption film underlying the capture layer. The biological material is situated on the capture layer. The capture layer may be configured to capture the biological material in any of the methods described above (e.g., mechanically, chemically, electrostatically, hydrophilic and/or hydrophobic interactions, combinations thereof, or the like). In this embodiment, the carrier is transparent to certain radiation such that for example laser radiation focused from the backside of the carrier onto the desorption film causes the sample to be released into the carrier gas flow and into the gas conduit. The desorption film can absorb the radiation to cause release of the desorption film and/or the biological sample. In some embodiments, the desorption film is thin. In some embodiments, the desorption film can be 100 nm thick, or it can be up to 1 micrometer thick. The laser light properties (wavelength, pulse duration) may be selected to provide absorption of a large portion of the laser energy into the film. The film can be made as thin as possible to minimize the energy needed for ablation of the film. Some materials and laser parameters might support absorption of the energy into an even thinner layers such as 10 nm or 30 nm. The desorption film may be various forms of plastics (such as PEN, PMMA, Kapton, etc.) and may be configured to absorb energy from UV lasers. Optionally, the desorption film may be triazene polymer or metallic layers. In further embodiments, the desorption film may be precut such that the desorption film is separated from adjacent desorption films associated with an adjacent pixel. In some embodiments, the desorption film may be precut prior to sample lifting using a laser—which could be a separate or the same laser than the laser used to heat or ablate the desorption layer during sample lifting. The precut desorption film may reduce the amount of energy required for lifting the sample into the gas phase and may thereby reduce the possibility of vaporizing or damaging the sample during lifting (e.g., via laser ablation or heating of the desorption film). Additionally, while not shown, a cushion layer may be disposed between the desorption layer and the capture layer. For instance, a thicker layer of plastic can be deposited on top of desorption/ablation layer. The cushion layer can be 1 micrometer thick while the ablation layer can be 100 nm. In this case the velocity and acceleration of the ablation layer will be reduced (cushioned) by about 10× when it propagates to the biological material due to inertia of the cushion layer. With the cushion layer it may be desirable to make it such that the area being lifted easily separates from the bulk or remainder of the cushion layer. Pre-cutting or patterning of the cushion layer can be useful.

The cushion layer may be provided to further protect the biological sample during lifting of the biological sample. For example, if the desorption layer is ablated to eject the biological sample from the support, the cushion layer may be configured to absorb the excess energy from the ablation to protect the biological sample during ejection.

Figure 7:
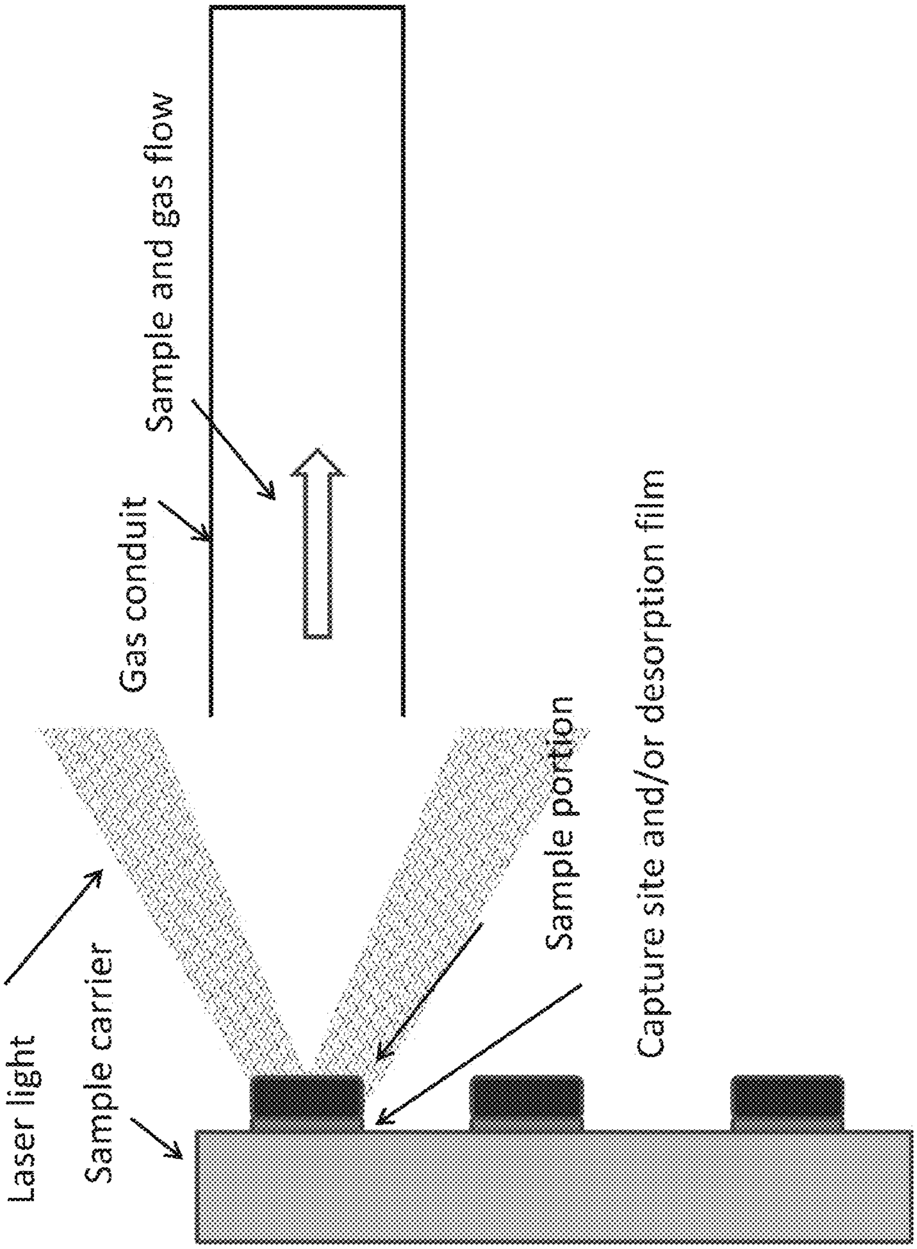
FIG. 7 shows a structured biological sample and associated carrier configured for laser desorption according to certain embodiments. The properties of laser light are chosen so that the light can pass through the sample portion with minimal damage yet cause thermal deposition at the capture site (for instance via explosion of desorption film)

FIG. 7 shows an alternative configuration in which radiation such as laser radiation is directed onto the front side of the sample. The laser radiation penetrates the biological sample and is absorbed the desorption film thereby causing the sample to be released from the capture site. The properties of the laser radiation are selected so that the biological sample remains intact and is not itself vaporized or ablated by the laser radiation.

In certain embodiments, a biological sample can be released or desorbed from a discrete site using nano-heaters, bubble jets, piezoelectrics, ultrasonics, electrostatics, or a combination of any of the foregoing.

Each, or a combination, of these techniques permits ordered detachment of sample material from the sample carrier. However, often, the location on the sample that is of interest does not represent a discrete entity, such as a lone cell, at a discrete site which can be easily lifted in isolation. Instead, the cell of interest may be surrounded by other cells or material, of which analysis is not required or desired. Trying to perform desorption (e.g. lifting) of the location of interest may therefore desorb both the cell of interest and surrounding material together. Atoms, such as labelling atoms which are used in elemental tags (see discussion below), from the surrounding area of the sample (e.g. from other cells which have been labelled) that are carried in a desorbed slug of material in addition to the specific location (e.g. cell) of interest could therefore contaminate the reading for the location of interest.

A solution to this problem is provided by the invention whereby the techniques of ablation and desorption (such as by lifting) can be combined in a single method. For example, to perform precise desorption of a location (e.g. cell) of interest on a biological sample, e.g. a tissue section sample or cell suspension dispersion, on the sample carrier, laser ablation can be used to ablate the area around the cell of interest to clear it of other material. After clearing the surrounding area by ablation, the location of interest can then be desorbed from the sample carrier, and then ionized and analyzed by mass spectrometry in line with standard mass cytometry or mass spectrometry procedures. In line with the above discussion, thermal, photolytic, chemical, or physical techniques can be used to desorb material from a location of interest, optionally after ablation has been used to clear the area surrounding the location that will be desorbed. Often, lifting will be employed, to separate the slug of material from the sample carrier (e.g. a sample carrier which has been coated with a desorption film to assist the lifting procedure, as discussed above with regard to desorption from discrete sites). The slug desorbed from the sample e.g. after clearing, is thus akin to the "pixel" discussed elsewhere herein with regard to material desorbed from discrete sites on structured sample carriers.

Figures 8A, 8B, 8C, 8D:
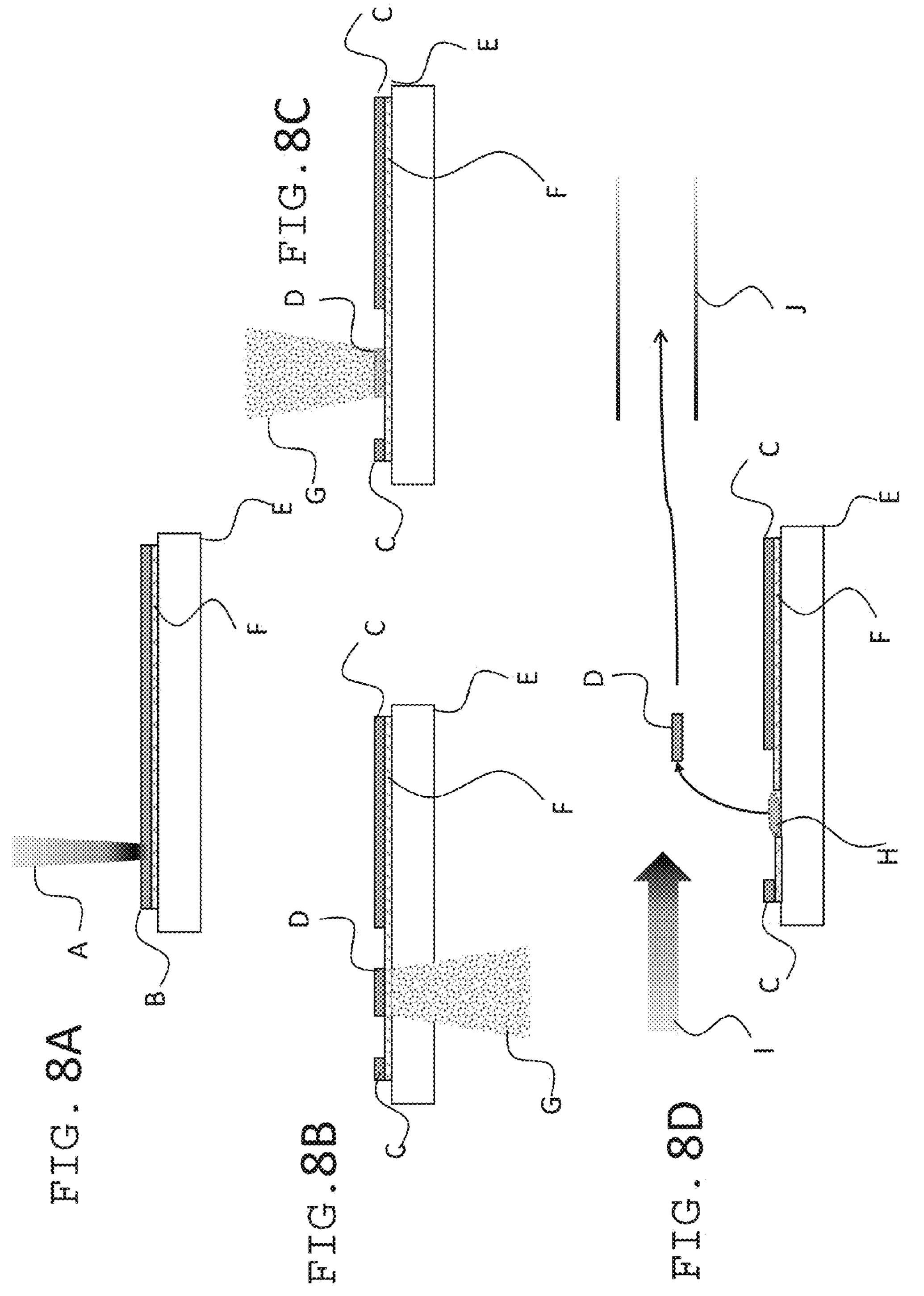
FIG. 8A to FIG. 8D shows ablation and desorption to analyze a location of interest on a biological sample.

FIG. 8 is a schematic of the steps of the combined ablation and lifting method. In FIG. 8A, first laser radiation (A) is directed on the sample (B), which ablates that part of the sample (as indicated by the gap between sample fragments (C) and the slug of material to be analyzed (D), in FIGS. 8B and 8C). The sample (B) is on a sample carrier (E) and between the sample and the carrier is a functionalized layer (F) of the type discussed in the preceding paragraphs, such as a desorption film coating, which assists the desorption of sample material from the surface of carrier. FIGS. 8B and 8C illustrate the same step—the irradiation of the functionalized layer (F) with laser radiation (G). FIGS. 8B and 8C are alternative modes of irradiation. 8B shows irradiation of the functionalized layer (F) through the sample carrier (E), whereas 4C shows irradiation of the functionalized layer (F) through the sample material to be desorbed (D). FIG. 8D illustrates the production of a gas (H) by the functionalized layer (F) following irradiation which ejects the slug of sample material (D) into the gas phase, wherein it is carried by the flow of gas (I) into the conduit (J) leading to the ionization system. In some instances, there is no production of gas by the functionalized layer to eject the slug of sample material, and instead another kind of laser-induced desorption occurs when the functionalized layer, such as a desorption film, absorbs laser radiation.

Accordingly, the invention provides a method of analyzing a sample comprising:

(i) performing laser ablation of a sample using laser radiation;

(ii) desorbing a slug of sample material using laser radiation; and (iii) ionizing the slug of sample material and detecting atoms in the slug by mass spectrometry.

In some embodiments, the ablation of the sample generates one or more plumes of sample material produced, and wherein the plumes are individually ionized and the atoms in the plume detected by mass spectrometry. In some embodiments, the sample is on a sample carrier comprising a functionalized layer, and laser radiation targets the functional layer, of the kind discussed above (such as a desorption film), in order to cause the desorption of the slug of sample material that separates it from the sample (i.e. lifting).

In some embodiments of the invention, the parts of the sample that are removed by desorption and by ablation may be different. For example, where there is a cluster of cells, ablation (such as with subcellular resolution) may be performed, to enable the imaging of all cells in the cluster (e.g. where desorbing the sample material could remove multiple cells at once, which may not be desired where cell-by-cell analysis is required). On the same sample, however, there may be cells which are spaced apart from the other cells, and so can be lifted. In some embodiments, step (ii) is performed before step (i).

In some embodiments, the sample is a biological sample, such as a tissue section, or a cell solution dispersed on the slide (and optionally fixed). In some embodiments, prior to step (i), the method comprises the additional step of labelling a plurality of different target molecules in the sample with one or more different labelling atoms, to provide a labelled sample. The labelling step thereby enables imaging mass cytometry, in addition to imaging mass spectrometry.

In some embodiments, the laser ablation is used to ablate the material around a location of interest to clear the surrounding area before the sample material at the location of interest is desorbed as a slug of material (e.g. by lifting). This slug of material is then analyzed, e.g. in the same way as the pixels discussed elsewhere herein, generated when structured sample carriers are employed.

The location of interest can be identified by another technique before the laser ablation and desorption (e.g. by lifting) is performed. The inclusion of a camera (such as a charged coupled device image sensor based (CCD) camera or a CMOS camera or an active pixel sensor based camera), or any other light detecting means in an imaging mass spectrometer as described in the preceding sections is one way of enabling these techniques. The camera can be used to scan the sample to identify cells of particular interest or locations of particular interest (for example cells of a particular morphology). Once such locations have been identified, the locations can be lifted after laser pulses have been directed at the area around the location of interest to clear other material by ablation before the location (e.g. cell) is lifted. This process may be automated (where the system both identifies, ablates and lifts the location(s) of interest) or semi-automated process (where the user of the system, for example a clinical pathologist, identifies the location(s) of interest, following which the system then performs ablation and lifting in an automated fashion). This enables a significant increase in the speed at which analyses can be conducted, because instead of needing to ablate the entire sample to analyze particular cells, the cells of interest can be specifically ablated.

The camera can record the image from a confocal microscope. The identification may be by light microscopy, for example by examining cell morphology or cell size. Sometimes, the sample can be specifically labelled to identify the location(s) (e.g. cell(s)) of interest.

Often, fluorescent markers are used to specifically stain the cells of interest (such as by using labelled antibodies or labelled nucleic acids). These fluorescent makers can be used to stain specific cell populations (e.g. expressing certain genes and/or proteins) or specific morphological features on cells (such as the nucleus, or mitochondria) and when illuminated with an appropriate wavelength of light, these regions of the sample are specifically identifiable. In some instances, the absence of a particular kind fluorescence from a particular area may be characteristic. For instance, a first fluorescent label targeted to a cell membrane protein may be used to broadly identify cells, but then a second fluorescent label targeted to the ki67 antigen (encoded by the MKI67 gene) can discriminate between proliferating cells and non-proliferating cells. Thus by targeting cells which lack fluorescence from the second label fluorescent, non-replicating cells can be specifically targeted for analysis. In some embodiments, the systems described herein therefore can comprise a laser for exciting fluorophores in the labels used to label the sample. Alternatively, an LED light source can be used for exciting the fluorophores. Non confocal (e.g. wide field) fluorescent microscopy can also be used to identify certain regions of the biological sample, but with lower resolution than confocal microscopy.

When a laser is used to excite fluorophores for fluorescence microscopy, in some embodiments this laser is the same laser that generates the laser radiation used to ablate material from the biological sample and for lifting (desorption), but used at a fluence that is not sufficient to cause ablation or desorption of material from the sample. In some embodiments, the fluorophores are excited by a wavelength of laser radiation that is used for sample desorption. The laser radiation that excites the fluorophores may be provided by a different laser source from the ablation and/or lifting laser source(s).

By using an image sensor (such as a CCD detector or an active pixel sensor, e.g. a CMOS sensor), it is possible to entirely automate the process of identifying regions of interest and then ablating them, by using a control module (such as a computer or a programmed chip) which correlates the location of the fluorescence with the x,y coordinates of the sample and then directs the ablation laser radiation to the area surrounding that location before the cell at the location is lifted. As part of this process, in some embodiments, the first image taken by the image sensor has a low objective lens magnification (low numerical aperture), which permits a large area of the sample to be surveyed. Following this, a switch to an objective with a higher magnification can be used to home in on the particular features of interest that have been determined to fluoresce by higher magnification optical imaging. These features recorded to fluoresce may then be lifted. Using a lower numerical aperture lens first has the further advantage that the depth of field is increased, thus meaning features buried within the sample may be detected with greater sensitivity than screening with a higher numerical aperture lens from the outset.

In methods and systems in which fluorescent imaging is used, the emission path of fluorescent light from the sample to the camera may include one or more lenses and/or one or more optical filters. By including an optical filter adapted to pass a selected spectral bandwidth from one or more of the fluorescent labels, the system is adapted to handle chromatic aberrations associated with emissions from the fluorescent labels. Chromatic aberrations are the result of the failure of lenses to focus light of different wavelengths to the same focal point. Accordingly, by including an optical filter, the background in the optical system is reduced, and the resulting optical image is of higher resolution. A further way to minimize the amount of emitted light of undesired wavelengths that reaches the camera is to exploit chromatic aberration of lenses deliberately by using a series of lenses designed for the transmission and focus of light at the wavelength transmitted by the optical filter, akin to the system explained in WO 2005/121864.

A higher resolution optical image is advantageous in this coupling of optical techniques and lifting, because the accuracy of the optical image then determines the precision with which the ablating laser source can be directed to ablate the area surrounding the cell of interest.

Accordingly, the invention provides a method of performing mass cytometry on a sample comprising a plurality of cells, the method comprising steps of: (i) labelling a plurality of different target molecules in the sample with one or more different labelling atoms, to provide a labelled sample; (ii) illuminating the sample with light to identify one or more locations of interest; (iii) recording locational information of the one or more locations of interest on the sample; (iv) using the locational information of the locations of interest to desorb a slug of sample material from a location of interest, comprises first performing laser ablation to remove sample material surrounding the location of interest, before the slug of sample material is desorbed from the location using laser radiation; (v) ionizing the desorbed slug of sample material; and (vi) subjecting the ionised sample material to mass spectrometry, for detection of labelling atoms in the sample material.

The invention also provides a method of performing mass cytometry on a sample comprising a plurality of cells, the method comprising steps of: (i) labelling a plurality of different target molecules in the sample with one or more different labelling atoms and one or more fluorescent labels, to provide a labelled sample; (ii) illuminating the sample with light to excite the one or more fluorescent labels; (iii) recording locational information of one or more locations of the sample based on the pattern of fluorescence; (iv) using the locational information based on the pattern of fluorescence to desorb a slug of sample material from a location of interest, comprising first performing laser ablation to remove sample material surrounding the location of interest, before the slug of sample material is desorbed from the location; (v) ionizing the desorbed slug of sample material; and (vi) subjecting the ionised sample material to mass spectrometry, for detection of labelling atoms in the sample material.

In some embodiments of the methods described above, the sample is on a sample carrier (e.g. microscope slide or other appropriate solid platform from which the sample can be ablated or desorbed, typically without significant removal of atoms of the carrier). In some embodiments, the laser radiation used to desorb sample material is directed to the sample material through the sample carrier. In some embodiments, the slug of sample material is desorbed by lifting. In some embodiments, the sample is on a sample carrier which comprises a layer which absorbs laser radiation to assist lifting of the slug of sample material. Examples of suitable layers, which may be a desorption film coated on the surface of the sample carrier, include triazene polymer, such as shown in FIG. 1 of Doraiswamy et al., 2006, Applied Surface Science, 52: 4743-4747, or other polymers which evaporate on upon laser radiation.

In some embodiments, no data are recorded from the ablation performed to clear the area around the location to be desorbed (e.g. the cell of interest). In some embodiments, data is recorded from the ablation of the surrounding area. Useful information that can be obtained from the surrounding area includes what target molecules, such as proteins and RNA transcripts, are present in the surrounding cells and intercellular milieu. This may be of particular interest when imaging solid tissue samples, where direct cell-cell interactions are common, and what proteins etc. are expressed in the surrounding cells may be informative on the state of the cell of interest.

The invention also provides an imaging mass spectrometer or imaging mass cytometer, comprising a control module programmed to perform the methods set out in this section.

Gas Conduit

Following desorption (e.g. by lifting) of a biological sample from the carrier, the biological sample can be injected into a gas stream and subsequently introduced into an ionization source, for example an ICP torch, where the biological sample is ionized and the ions subsequently recorded by suitable mass spectrometry methods.

The carrier gas may be any suitable gas for use in mass cytometry or mass spectrometry including inert gases such as argon, helium, or a combination thereof.

The carrier gas can flow across the surface of a carrier and confined at one end into a narrow flow tube or channel. Much like a fluidic flow cytometer, the carrier gas and entrained biological sample can be gas dynamically focused such that individual pixels enter the ionization source, for example an ICP torch, one at a time.

The length of the gas conduit can be any suitable length with the objective of delivering desorbed biological sample from the carrier to the ionization source, for example an ICP source, of a mass cytometer or mass spectrometer. Based largely on practical considerations the length of the gas conduit can be from about 10 cm to about 40 cm.

The diameter of the gas conduit can be any suitable diameter, again with the objective of delivering desorbed biological sample from the carrier to the ionization source, for example an ICP source, of a mass cytometer or mass spectrometer. For example, in certain embodiments a gas conduit can have an inner diameter from about 0.2 mm to about 3 mm. It is desirable that the inner diameter of the gas conduit be sufficiently large to minimize clogging. The conduit can have a certain diameter throughout the most of its length but can also taper down to a smaller diameter near the ICP torch as commonly practiced for ICP torch injectors. Again, the dynamics along the gas conduit is established and manipulated to facilitate a continuous stream of discrete material pixels into the ICP source. Ideally the pixels will be located toward the center of the gas conduit where the gas velocity is a maximum and the change in velocity with position is minimized. In certain embodiments, the carrier gas flow through the conduit is characterized by laminar gas flow with a parabolic profile center along the axis of the gas conduit.

Mass Cytometry Analysis

In certain embodiments, a biological sample is labeled with an element tag. Element tags comprising metal polymer conjugates can provide highly multiplexed sensitive assays for biological material; the metal atoms are also termed labelling atoms. The element tags can be conjugated to affinity molecules such as antibodies, which can be used for quantitative proteomics and genomics of biological samples. Element tags are described, for example in U.S. Application No. 2008/0003616, which is incorporated by reference in its entirety. Analysis of biological material using element tags is described, for example, in U.S. Application Publication Nos. 2010/0144056, 2012/0061561, 2014/0120550, and 2014/0121117, and WO 2014/169294, each of which is incorporated by reference in its entirety. In general, the materials and methods disclosed in these publications can be applied to the embodiments provided by the present disclosure, with the primary difference being that in the publications, the biological material is ablated or vaporized and transferred as a vapor plume from the sample carrier to the ionization source, for example an ICP source. In contrast, in the embodiments provided by the present disclosure, the biological material is desorbed (e.g., lifted, released, or ejected) from the carrier surface as an un-vaporized material pixel, which becomes entrained in a carrier gas flow to bring the material sample to the ionization source, for example an ICP source.

Labelling of the Biological Sample

In some embodiments, as described above, the apparatus and methods of the invention detect atoms that have been added to a sample (i.e. which are not normally present). As noted above such atoms are called labelling atoms. The sample is typically a biological sample comprising cells, and the labelling atoms are used to label target molecules in the cells/on the cell surface. In some embodiments, simultaneous detection of many more than one labelling atom, permitting multiplex label detection e.g. at least 3, 4, 5, 10, 20, 30, 32, 40, 50 or even 100 different labelling atoms is enabled. Labelling atoms can also be used in a combinatorial manner to even further increase the number of distinguishable labels. By labelling different targets with different labelling atoms it is possible to determine the presence of multiple targets on a single cell.

Labelling atoms that can be used with the invention include any species that are detectable by MS and that are substantially absent from the unlabelled sample. Thus, for instance, $^{12}C$ atoms (carbon 12) would be unsuitable as labelling atoms because they are naturally abundant, whereas $^{11}C$ could in theory be used because it is an artificial isotope which does not occur naturally. In preferred embodiments, however, the labelling atoms are transition metals, such as the rare earth metals (the 15 lanthanides, plus scandium and yttrium). These 17 elements provide many different isotopes which can be easily distinguished by MS. A wide variety of these elements are available in the form of enriched isotopes e.g. samarium has 6 stable isotopes, and neodymium has 7 stable isotopes, all of which are available in enriched form. The 15 lanthanide elements provide at least 37 isotopes that have non-redundantly unique masses. Examples of elements that are suitable for use as labelling atoms include Lanthanum (La), Cerium (Ce), Praseodymium (Pr), Neodymium (Nd), Promethium (Pm), Samarium (Sm), Europium (Eu), Gadolinium, (Gd), Terbium (Tb), Dysprosium (Dy), Holmium (Ho), Erbium (Er), Thulium (Tm), Ytterbium (Yb), Lutetium (Lu), Scandium (Sc), and Yttrium (Y). In addition to rare earth metals, other metal atoms are suitable for detection by MS e.g. gold (Au), platinum (Pt), iridium (Ir), rhodium (Rh), bismuth (Bi), etc. The use of radioactive isotopes is not preferred as they are less convenient to handle and are unstable e.g. Pm is not a preferred labelling atom among the lanthanides.

In order to facilitate time of flight analysis it is helpful to use labelling atoms with an atomic mass within the range 80-250 e.g. within the range 80-210, or within the range 100-200. This range includes all of the lanthanides, but excludes Sc and Y. The range of 100-200 permits a theoretical 101-plex analysis by using different labelling atoms, while permitting the invention to take advantage of the high spectral scan rate of TOF MS. As mentioned above, by choosing labelling atoms whose masses lie in a window above those seen in an unlabelled sample (e.g. within the range of 100-200), TOF detection can be used to provide rapid analyses at biologically significant levels.

Labelling the particles generally requires that the labelling atoms are attached to one member of a specific binding pair (sbp). This labelled sbp is contacted with a sample such that it can interact with the other member of the sbp (the target sbp member) if it is present, thereby localizing the labelling atom to a target molecule in the sample. The method of the invention then detects the presence of the labelling atom on a particle as it is analyzed by the mass cytometer. Rare earth metals and other labelling atoms can be conjugated to sbp members by known techniques e.g. Bruckner et al. (2013) Anal. Chem. 86:585-91 describes the attachment of lanthanide atoms to oligonucleotide probes for MS detection, Gao & Yu (2007) Biosensor Bioelectronics 22:933-40 describes the use of ruthenium to label oligonucleotides, and Fluidigm Canada sells the MaxPar™ metal labelling kits which can be used to conjugate over 30 different labelling atoms to proteins (including antibodies).

Various numbers of labelling atoms can be attached to a single sbp member, and greater sensitivity can be achieved when more labelling atoms are attached to any sbp member. For example greater than 10, 20, 30, 40, 50, 60, 70, 80, 90 or 100 labelling atoms can be attached to a sbp member. For example, monodisperse polymers containing multiple monomer units may be used, each containing a chelator such as DTPA. DTPA, for example, binds 3+ lanthanide ions with a dissociation constant of about $10^{-6}$ M. These polymers can terminate in a thiol-reactive group (e.g. maleimide) which can be used for attaching to a sbp member. For example the thiol-reactive group may bind to the Fc region of an antibody. Other functional groups can also be used for conjugation of these polymers e.g. amine-reactive groups such as N-hydroxy succinimide esters, or groups reactive against carboxyls or against an antibody's glycosylation. Any number of polymers may bind to each sbp member. Specific examples of polymers that may be used include straight-chain ("X8") polymers or third-generation dendritic ("DN3") polymers, both available as MaxPar™ reagents. Use of metal nanoparticles can also be used to increase the number of atoms in a label.

As mentioned above, labelling atoms are attached to a sbp member, and this labelled sbp member is contacted with the sample where it can find the target sbp member (if present), thereby forming a labelled sbp. The labelled sbp member can comprise any chemical structure that is suitable for attaching to a labelling atom and then for detection according to the invention.

In general terms, methods of the invention can be based on any sbp which is already known for use in determining the presence of target molecules in samples (e.g. as used in IHC or fluorescence in situ hybridisation, FISH) or fluorescence-based flow cytometry, but the sbp member which is contacted with the sample will carry a labelling atom which is detectable by MS. Thus the invention can readily be implemented by using available flow cytometry reagents, merely by modifying the labels which have previously been used e.g. to modify a FISH probe to carry a label which can be detected by MS.

The sbp may comprise any of the following: a nucleic acid duplex; an antibody/antigen complex; a receptor/ligand pair; or an aptamer/target pair. Thus a labelling atom can be attached to a nucleic acid probe which is then contacted with a sample so that the probe can hybridize to complementary nucleic acid(s) therein e.g. to form a DNA/DNA duplex, a DNA/RNA duplex, or a RNA/RNA duplex. Similarly, a labelling atom can be attached to an antibody which is then contacted with a sample so that it can bind to its antigen. A labelling atom can be attached to a ligand which is then contacted with a sample so that it can bind to its receptor. A labelling atom can be attached to an aptamer ligand which is then contacted with a sample so that it can bind to its target. Thus labelled sbp members can be used to detect a variety of target molecules in a sample, including DNA sequences, RNA sequences, proteins, sugars, lipids, or metabolites.

In a typical embodiment of the invention the labelled sbp member is an antibody. Labelling of the antibody can be achieved through conjugation of one or more labelling atom binding molecules to the antibody, for example using the MaxPar™ conjugation kit as described above. The target molecule of an antibody is called its antigen, and may be a protein, carbohydrate, nucleic acid etc. Antibodies which recognize cellular proteins that are useful for mass cytometry are already widely available for IHC usage, and by using labelling atoms instead of current labelling techniques (e.g. fluorescence) these known antibodies can be readily adapted for use in methods of the invention, but with the benefit of increasing multiplexing capability. Antibodies used with the invention can recognize targets on the cell surface or targets within a cell. Antibodies can recognize a variety of targets e.g. they can specifically recognize individual proteins, or can recognize multiple related proteins which share common epitopes, or can recognize specific post-translational modifications on proteins (e.g. to distinguish between tyrosine and phospho-tyrosine on a protein of interest, to distinguish between lysine and acetyl-lysine, to detect ubiquitination, etc.). After binding to its target, labelling atom(s) conjugated to an antibody can be detected to reveal the presence of that target in a sample.

The labelled sbp member will usually interact directly with a target sbp member in the sample. In some embodiments, however, it is possible for the labelled sbp member to interact with a target sbp member indirectly e.g. a primary antibody may bind to the target sbp member, and a labelled secondary antibody can then bind to the primary antibody, in the manner of a sandwich assay. Usually, however, the invention relies on direct interactions, as this can be achieved more easily and permits higher multiplexing. In both cases, however, a sample is contacted with a sbp member which can bind to a target sbp member in the sample, and at a later stage label attached to the target sbp member is detected.

One feature of the invention is its ability to detect multiple (e.g. 10 or more, and even up to 100 or more) different target sbp members in a sample e.g. to detect multiple different proteins and/or multiple different nucleic acid sequences on particles such as cells or beads. To permit differential detection of these target sbp members their respective sbp members should carry different labelling atoms such that their signals can be distinguished by MS. For instance, where ten different proteins are being detected, ten different antibodies (each specific for a different target protein) can be used, each of which carries a unique label, such that signals from the different antibodies can be distinguished. In some embodiments, it is desirable to use multiple different antibodies against a single target e.g. which recognize different epitopes on the same protein. Thus a method may use more antibodies than targets due to redundancy of this type. In general, however, the invention will use a plurality of different labelling atoms to detect a plurality of different targets.

If more than one labelled antibody is used with the invention, it is preferable that the antibodies should have similar affinities for their respective antigens, as this helps to ensure that the relationship between the quantity of labelling atoms detected by MS and the abundance of the target antigen will be more consistent across different sbps (particularly at high scanning frequencies).

If a target sbp member is located intracellularly, it will typically be necessary to permeabilise cell membranes before or during contacting of the sample with the labels. For example when the target is a DNA sequence but the labelled sbp member cannot penetrate the membranes of live cells, the cells of the sample can be fixed and permeabilised. The labelled sbp member can then enter the cell and form a sbp with the target sbp member.

Usually, a method of the invention will detect at least one intracellular target and at least one cell surface target. In some embodiments, however, the invention can be used to detect a plurality of cell surface targets while ignoring intracellular targets. Overall, the choice of targets will be determined by the information which is desired from the method.

Accordingly, in some embodiments, the methods of analysis described above comprise the step of labelling a sample with at least one labelling atom. This atom can then be detected using the methods described above.

Figure 9:
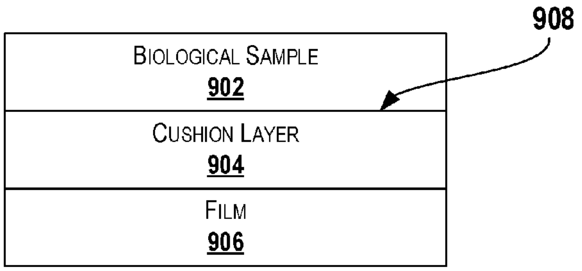
FIG. 9 is a block diagram depicting a cushion layer disposed between a biological sample and a film according to certain aspects of the present disclosure.

FIG. 9 is a block diagram depicting a cushion layer 904 disposed between a biological sample 902 and a film 906 according to certain aspects of the present disclosure. A surface 908 of the cushion layer 904 may be modified to preferentially capture a target biological sample.

Figure 10:
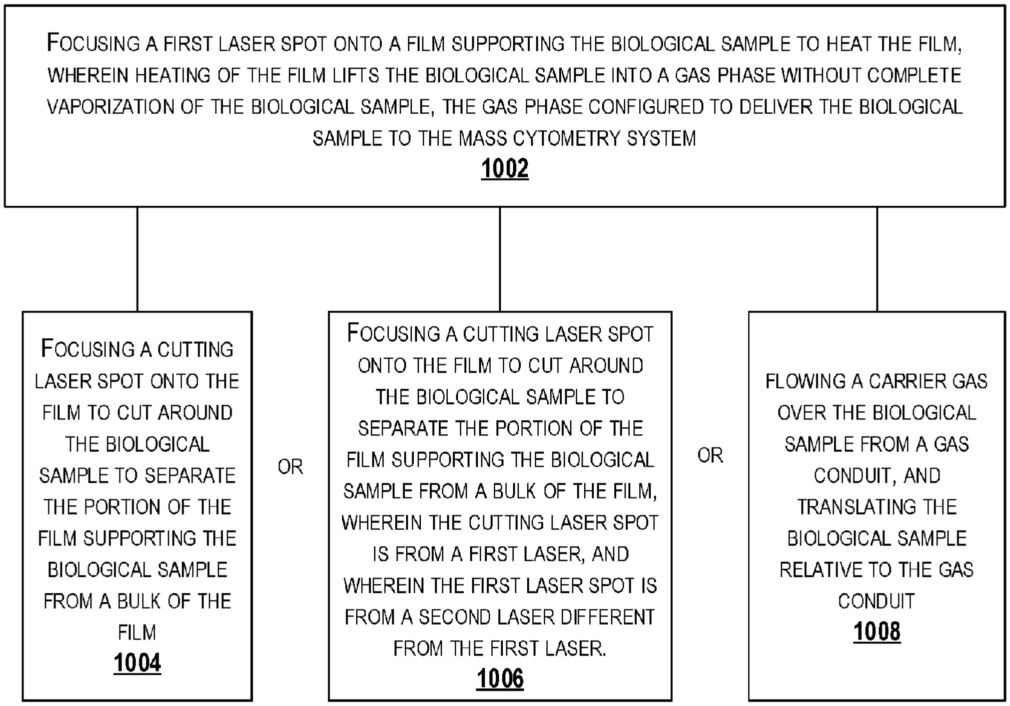
FIG. 10 is a flowchart depicting a method of delivering a biological sample into a mass cytometry system.

FIG. 10 is a flowchart depicting a method of delivering a biological sample into a mass cytometry system. At block 1002, the method comprises focusing a first laser spot onto a film supporting the biological sample to heat the film, wherein heating of the film lifts the biological sample into a gas phase without complete vaporization of the biological sample, the gas phase configured to deliver the biological sample to the mass cytometry system. At block 1004, the method comprises focusing a cutting laser spot onto the film to cut around the biological sample to separate the portion of the film supporting the biological sample from a bulk of the film. Alternatively, at block 1006, the method further comprises focusing a cutting laser spot onto the film to cut around the biological sample to separate the portion of the film supporting the biological sample from a bulk of the film, wherein the cutting laser spot is from a first laser, and wherein the first laser spot is from a second laser different from the first laser. At block 1008, the method can comprise flowing a carrier gas over the biological sample from a gas conduit, and translating the biological sample relative to the gas conduit.

FIG. 11 is a flowchart depicting a method of analyzing a sample. At block 1102, the method comprises performing laser ablation of a sample using laser radiation. At block 1106, the method comprises desorbing a slug of sample material. At block 1108, the method comprises ionizing the slug of sample material and detecting atoms in the slug by mass spectrometry. At block 1104, the method comprises using laser ablation to ablate the material around a location of interest to clear a surrounding area before the sample material at the location of interest is desorbed from a sample carrier as a slug of material.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of delivering a biological sample into a mass cytometry system, the method comprising:

focusing a cutting laser spot onto a film to cut around the biological sample to separate the portion of the film supporting the biological sample from a bulk of the film; and focusing an additional laser spot onto the film supporting the biological sample to heat the film, wherein heating of the film lifts the biological sample into a gas phase without complete vaporization of the biological sample, the gas phase configured to deliver the biological sample to the mass cytometry system.

2. The method of claim 1, wherein the film is coupled with a substrate, and wherein the film comprises a plurality of separate portions of film at discrete spaced apart sites on the substrate.

3. The method of claim 2, wherein the plurality of separate portions of film define a plurality of cell capture sites, wherein the cell capture sites are configured to capture only a single cell.

4. The method of claim 2, wherein a surface of gaps between the plurality of separate portions of film are modified to repel the biological sample.

5. The method of claim 1, wherein the additional laser spot is focused onto the film supporting the biological sample to ablate the film.

6. The method of claim 5, wherein a cushion layer is disposed between the biological sample and the film, the cushion layer configured to absorb energy from the ablation of the film to limit damage to the biological sample from the ablation of the film.

7. The method of claim 6, wherein a surface of the cushion layer is modified to preferentially capture a target biological sample.

8. The method of claim 1, wherein the cutting laser spot is from a first laser, and wherein the additional laser spot is from a second laser different from the first laser.

9. The method of claim 1, further comprising flowing a carrier gas over the biological sample from a gas conduit, and translating the biological sample relative to the gas conduit.

10. The method of claim 1, wherein the biological sample is applied to a sample carrier, and wherein the sample carrier includes a corrugated surface.

11. The method of claim 10, wherein the corrugated surface of the sample carrier includes raised edges configured to cut a tissue section into one or more individual regions.

12. A method of analyzing a sample comprising:

(i) performing laser ablation of a sample using laser radiation, wherein performing laser ablation includes ablating material around a location of interest to clear a surrounding area before the sample material at the location of interest is desorbed from a sample carrier as a slug of sample material;

(ii) desorbing the slug of sample material; and (iii) ionizing the slug of sample material and detecting atoms in the slug by mass spectrometry.

13. The method of claim 12, wherein the sample is on a sample carrier.

14. The method of claim 13, wherein laser radiation is directed through the sample carrier to desorb the slug of sample material from the sample carrier.

* * * * *